(12) United States Patent
Mauger et al.

(10) Patent No.: US 10,806,405 B2
(45) Date of Patent: Oct. 20, 2020

(54) SPEECH PRODUCTION AND THE MANAGEMENT/PREDICTION OF HEARING LOSS

(71) Applicants: Stefan Jozef Mauger, East Melbourne (AU); Kieran Reed, Macquarie University (AU); John Michael Heasman, East Melbourne (AU)

(72) Inventors: Stefan Jozef Mauger, East Melbourne (AU); Kieran Reed, Macquarie University (AU); John Michael Heasman, East Melbourne (AU)

(73) Assignee: Cochlear Limited, Macquarie University, NSW (AU)

( * ) Notice: Subject to any disclaimer, the term of this patent is extended or adjusted under 35 U.S.C. 154(b) by 581 days.

(21) Appl. No.: 15/376,975

(22) Filed: Dec. 13, 2016

(65) Prior Publication Data

US 2018/0160984 A1    Jun. 14, 2018

(51) Int. Cl.
| | | |
|---|---|---|
| A61B 5/00 | (2006.01) |
| G10L 25/30 | (2013.01) |
| A61B 5/12 | (2006.01) |
| G06N 3/08 | (2006.01) |

(52) U.S. Cl.
CPC ............ *A61B 5/7275* (2013.01); *A61B 5/125* (2013.01); *A61B 5/4803* (2013.01); *A61B 5/486* (2013.01); *A61B 5/7267* (2013.01); *G06N 3/08* (2013.01); *G10L 25/30* (2013.01)

(58) Field of Classification Search
CPC ....... A61B 5/7275; A61B 5/125; A61B 5/486; A61B 5/7267; G06N 3/02; G10L 25/30
See application file for complete search history.

(56) References Cited

U.S. PATENT DOCUMENTS

| | | |
|---|---|---|
| 4,803,732 A | 2/1989 | Dillon |
| 5,278,912 A | 1/1994 | Waldhauer |
| 5,729,658 A | 3/1998 | Hou et al. |
| 7,020,581 B2 | 3/2006 | Dittberner |
| 8,147,422 B2 | 4/2012 | Kuo et al. |
| 2010/0106218 A1 | 4/2010 | Botros |
| 2013/0204325 A1 | 8/2013 | Botros |
| 2014/0249824 A1 | 9/2014 | MacAuslan |

(Continued)

FOREIGN PATENT DOCUMENTS

WO     2016011189 A1    1/2016

OTHER PUBLICATIONS

Aliabadi et al. 'Prediction of hearing loss among the noise-exposed workers in a steel factor using artificial intelligence approach' Int Arch Occup Environ Health (2015) 88:779-787; Published Online 2014 (Year: 2014).*

(Continued)

*Primary Examiner* — Patrick Fernandes
(74) *Attorney, Agent, or Firm* — Pilloff Passino & Cosenza LLP; Martin J. Cosenza

(57) ABSTRACT

A method, including obtaining hearing data and speech data for a statistically significant number of individuals, and analyzing the obtained hearing data and speech data using a neural network to develop a predictive algorithm for hearing loss based on the results of the analysis, wherein the predictive algorithm predicts hearing loss based on input indicative of speech of a hearing impaired person who is not one of the individuals.

18 Claims, 18 Drawing Sheets

(56) References Cited

U.S. PATENT DOCUMENTS

2016/0078863 A1 3/2016 Chung et al.
2016/0104486 A1 4/2016 Penilla et al.
2016/0135732 A1 5/2016 Poellabauer et al.

OTHER PUBLICATIONS

Tomblin et al. 'The Influence of Hearing Aids on the Speech and Language Development of Children With Hearing Loss' JAMA Otolaryngol Head Neck Surg. May 1, 2104; 140(5): 403-409 (Year: 2014).*

Shilpi Banerjee, "The Compression Handbook, Third Edition, An overview of the characteristics and applications of compression amplification," Jan. 2011, Starkey Hearing Research & Technology.

Harlan Lane et al., "Speech deterioration in postlingually deafened adults," Journal of the Acoustical Society of America, Feb. 1991, pp. 859-866, vol. 89, No. 2.

Meysam Asgari et al., "Inferring Clinical Depression From Speech and Spoken Utterances," Sep. 2014, IEEE International Workshop on Machine Learning for Signal Processing (MLSP).

* cited by examiner

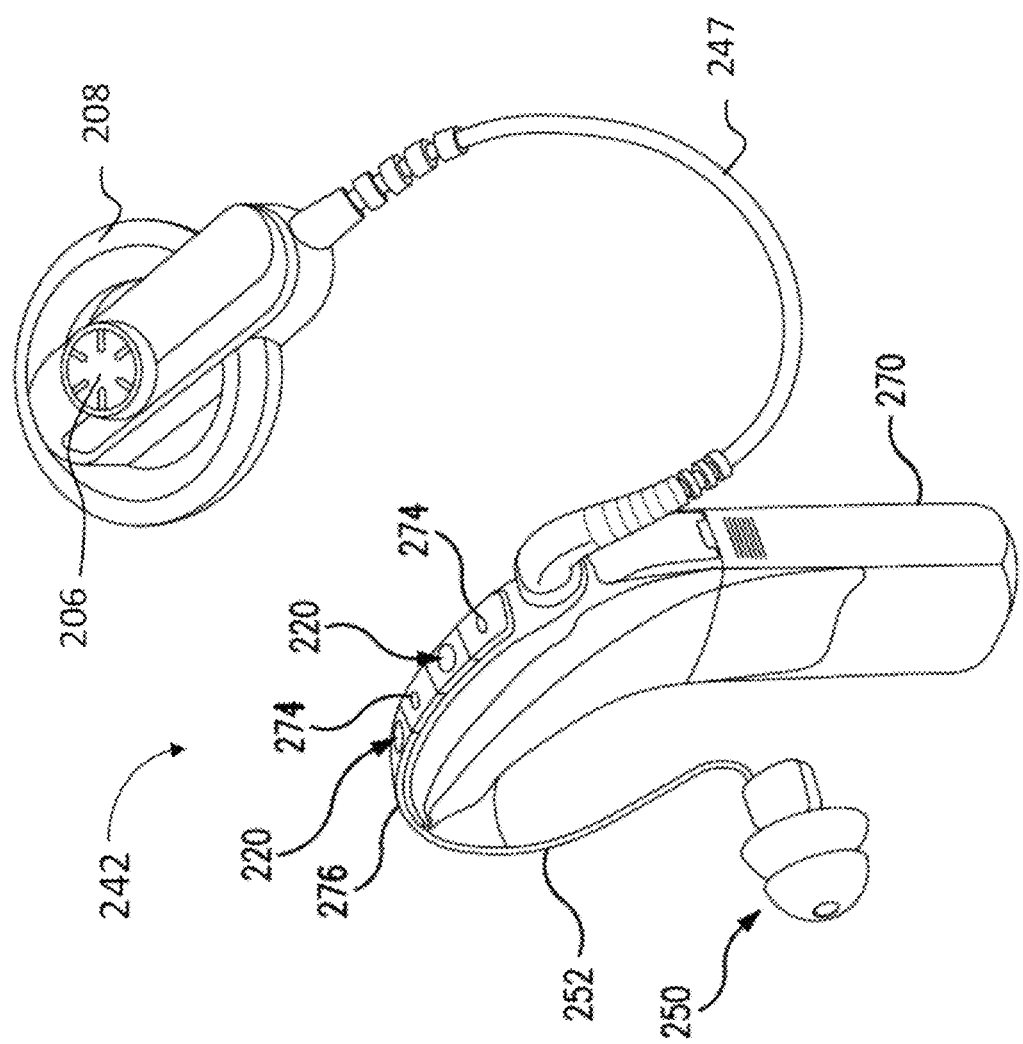

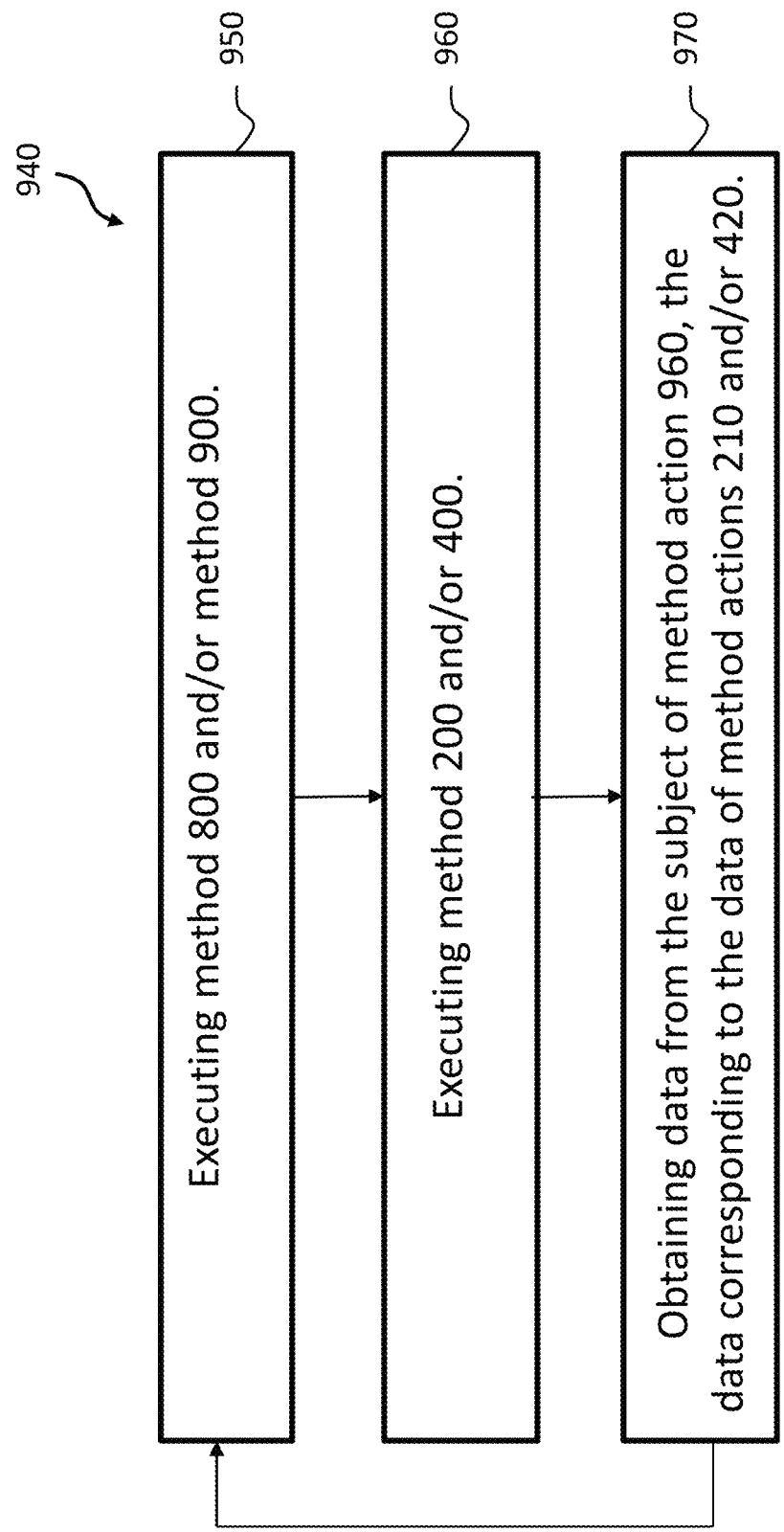

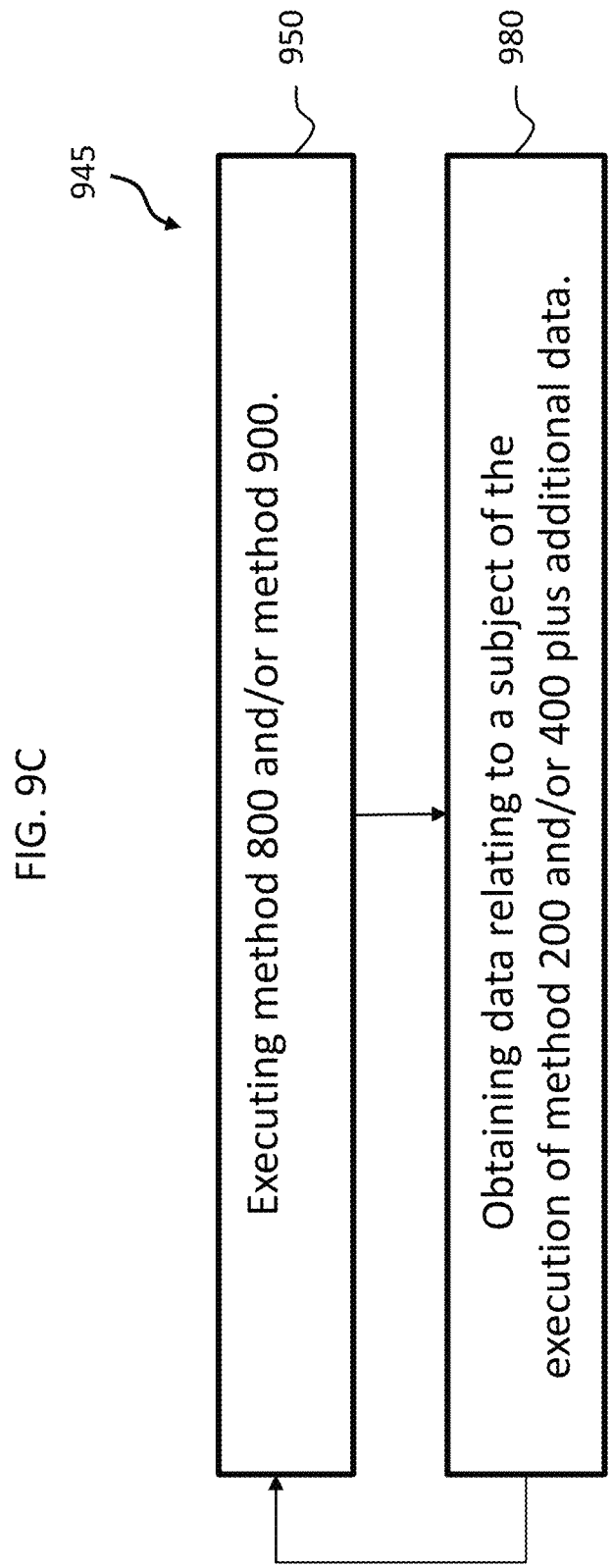

SPEECH PRODUCTION AND THE MANAGEMENT/PREDICTION OF HEARING LOSS

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In accordance with an exemplary embodiment, there is a method, comprising obtaining hearing data and speech data for a statistically significant number of individuals, and analyzing the obtained hearing data and speech data using machine learning to develop a predictive algorithm for hearing loss based on the results of the analysis, wherein the predictive algorithm predicts hearing loss based on input indicative of speech of a hearing impaired person who is not one of the individuals.

In accordance with another embodiment, there is a method, comprising obtaining data based on speech of a person; and analyzing the obtained data based on speech using a code of and/or from a machine learning algorithm to develop data regarding hearing loss of the person, wherein the machine learning algorithm is a trained system trained based on a statistically significant population of hearing impaired persons In accordance with another exemplary embodiment, there is a method, comprising obtaining data based on speech of a person, and developing a prescription and/or a fitting regime for a hearing prosthesis based on the obtained data.

BRIEF DESCRIPTION OF THE DRAWINGS

Embodiments are described below with reference to the attached drawings, in which:

FIG. 1B is another view of the exemplary multimodal hearing prosthesis presented in FIG. 1A;

DETAILED DESCRIPTION

Figure 1A:
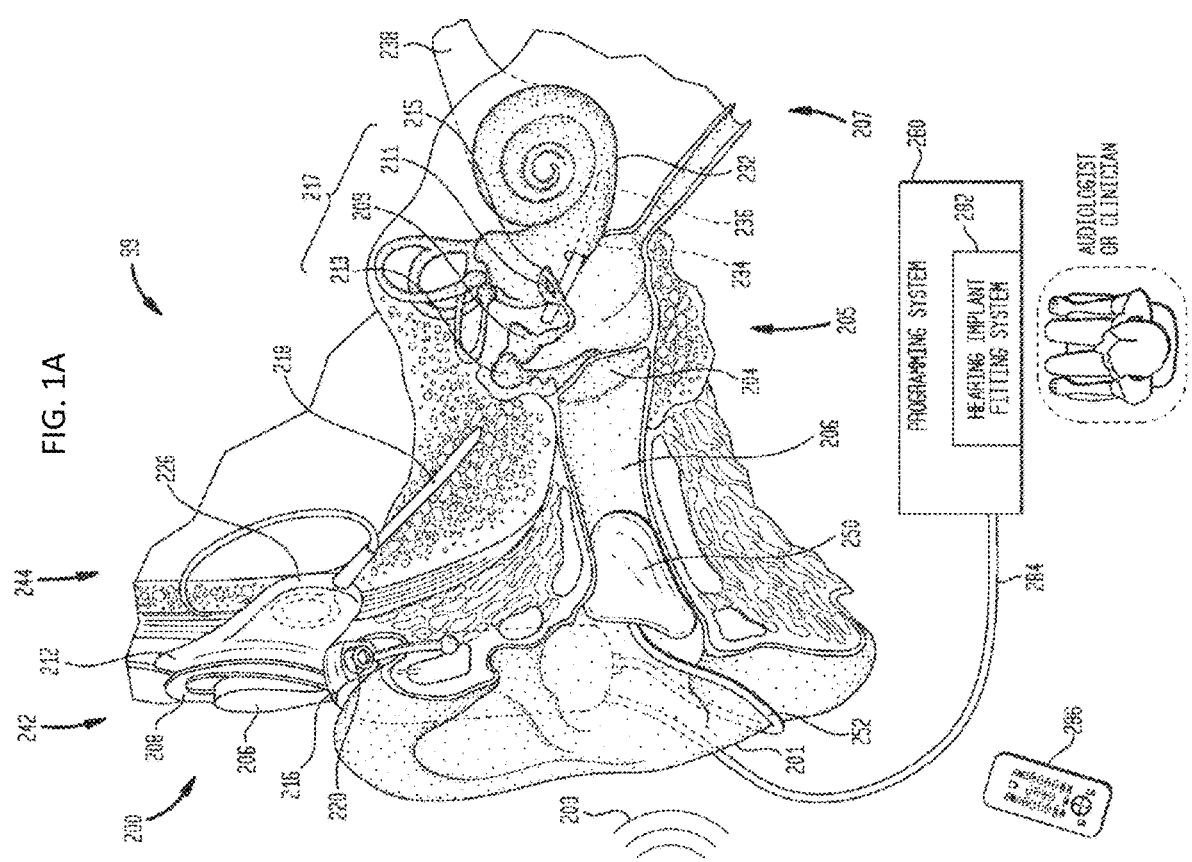
FIG. 1A is a perspective view of an exemplary multimodal hearing prosthesis according to an exemplary embodiment.

FIG. 1A is a perspective view of an exemplary multimodal prosthesis in which the present invention may be implemented. The ear 99 includes outer ear 201, middle ear 205, and inner ear 207 are described next below, followed by a description of an implanted multimodal system 200. Multimodal system 200 provides multiple types of stimulation, i.e., acoustic, electrical, and/or mechanical. These different stimulation modes may be applied ipsilaterally or contralaterally. In the embodiment shown in FIG. 1A, multimodal implant 200 provides acoustic and electrical stimulation, although other combinations of modes can be implemented in some embodiments. By way of example and not by way of limitation, a middle-ear implant can be utilized in combination with the cochlear implant, a bone conduction device can be utilized in combination with the cochlear implant, etc.

In a person with normal hearing or a recipient with residual hearing, an acoustic pressure or sound wave 203 is collected by outer ear 201 (that is, the auricle) and channeled into and through ear canal 206. Disposed across the distal end of ear canal 206 is a tympanic membrane 204 which vibrates in response to acoustic wave 203. This vibration is coupled to the oval window, fenestra ovalis 215 through three bones of middle ear 205, collectively referred to as the ossicles 217 and comprising the malleus 213, the incus 209, and the stapes 211. Bones 213, 209, and 211 of middle ear 205 serve to filter and transfer acoustic wave 203, causing oval window 215 to articulate, or vibrate. Such vibration sets up waves of fluid motion within cochlea 232. Such fluid motion, in turn, activates tiny hair cells (not shown) that line the inside of cochlea 232. Activation of the hair cells causes appropriate nerve impulses to be transferred through the spiral ganglion cells (not shown) and auditory nerve 238 to the brain (not shown), where such pulses are perceived as sound.

In individuals with a hearing deficiency who may have some residual hearing, an implant or hearing instrument may improve that individual's ability to perceive sound. Multimodal prosthesis 200 may comprises external component assembly 242 which is directly or indirectly attached to the body of the recipient, and an internal component assembly 244 which is temporarily or permanently implanted in the recipient. External component assembly is also shown in FIG. 1B. In embodiments of the present invention, components in the external assembly 242 may be included as part of the implanted assembly 244, and vice versa. Also, embodiments of the present invention may be used with implanted multimodal system 200 which are fully implanted.

External assembly 242 typically comprises a sound transducer 220 for detecting sound, and for generating an electrical audio signal, typically an analog audio signal. In this illustrative embodiment, sound transducer 220 is a microphone. In alternative embodiments, sound transducer 220 can be any device now or later developed that can detect sound and generate electrical signals representative of such sound.

Figure 1C:
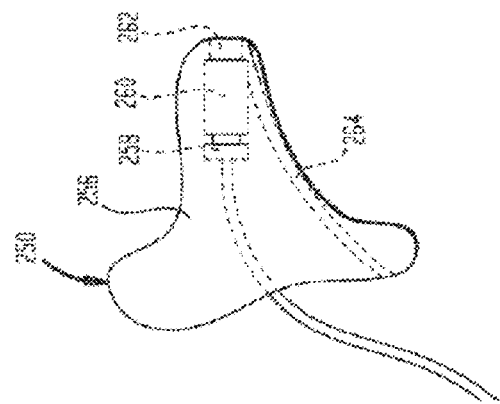
FIG. 1C provides additional details of the exemplary multimodal hearing prosthesis of FIG. 1B.

External assembly 242 also comprises a signal processing unit, a power source, and an external transmitter unit. External transmitter unit 206 comprises an external coil 208 and, preferably, a magnet 206 secured directly or indirectly to the external coil 208. Signal processing unit processes the output of microphone 220 that is positioned, in the depicted embodiment, by outer ear 201 of the recipient. Signal processing unit generates coded signals, referred to herein as a stimulation data signals, which are provided to external transmitter unit 206 via a cable 247 and to the receiver in the ear 250 via cable 252. FIG. 1C provides additional details of an exemplary receiver 250. The overall component containing the signal processing unit is, in this illustration, constructed and arranged so that it can fit behind outer ear 201 in a BTE (behind-the-ear) configuration, but may also be worn on different parts of the recipient's body or clothing.

In some embodiments, the signal processor may produce electrical stimulations alone, without generation of any acoustic stimulation beyond those that naturally enter the ear. While in still further embodiments, two signal processors may be used. One signal processor is used for generating electrical stimulations in conjunction with a second speech processor used for producing acoustic stimulations.

As shown in FIGS. 1B and 1C, a receiver in the ear 250 is connected to the signal processor through cable 252. Receiver in the ear 250 includes a housing 256, which may be a molding shaped to the recipient. Inside receiver in the ear 250 there is provided a capacitor 258, receiver 260 and protector 262. Also, there may be a vent shaft 264 (in some embodiments, this vent shaft is not included). Receiver in the ear may be an in-the-ear (ITE) or completely-in-canal (CIC) configuration.

Also, FIG. 1B shows a removable battery 270 directly attached to the body/spine of the BTE device. As seen, the BTE device in some embodiments control buttons 274. In addition, the BTE may house a power source, e.g., zinc-air batteries. The BTE device may have an indicator light 276 on the earhook to indicate operational status of signal processor. Examples of status indications include a flicker when receiving incoming sounds, low rate flashing when power source is low or high rate flashing for other problems.

Returning to FIG. 1A, internal components 244 comprise an internal receiver unit 212, a stimulator unit 226 and an electrode assembly 218. Internal receiver unit 212 comprises an internal transcutaneous transfer coil (not shown), and preferably, a magnet (also not shown) fixed relative to the internal coil. Internal receiver unit 212 and stimulator unit 226 are hermetically sealed within a biocompatible housing. The internal coil receives power and data from external coil 208. Cable or lead of electrode assembly 218 extends from stimulator unit 226 to cochlea 232 and terminates in an array 234 of electrodes 236. Electrical signals generated by stimulator unit 226 are applied by electrodes 236 to cochlea 232, thereby stimulating the auditory nerve 238.

In one embodiment, external coil 208 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 212 may be positioned in a recess of the temporal bone adjacent to outer ear 201 of the recipient.

As shown in FIG. 1A, multimodal system 200 is further configured to interoperate with a user interface 280 and an external processor 282 such as a personal computer, workstation, or the like, implementing, for example, a hearing implant fitting system. Although a cable 284 is shown in FIG. 1A between implant 200 and interface 280, a wireless RF communication may also be used along with remote 286.

While FIG. 1A shows a multimodal implant in the ipsilateral ear, in other embodiments of the present invention the multimodal implant may provide stimulation to both ears. For example, a signal processor may provide electrical stimulation to one ear and provide acoustical stimulation in the other ear.

Cochlea 232 is tonotopically mapped with each region of the cochlea being responsive to acoustic and/or stimulus signals in a particular frequency range. To accommodate this property of cochlea 232, the cochlear implant system includes an array of electrodes each constructed and arranged to deliver suitable stimulating signals to particular regions of the cochlea, each representing a different frequency component of a received audio signal 203. Signals generated by stimulator unit 226 are applied by electrodes of electrode array to cochlea 232, thereby stimulating the auditory nerve.

Typically, the electrode array of the cochlear implant includes a plurality of independent electrodes each of which can be independently stimulated. Low frequency sounds stimulate the basilar membrane most significantly at its apex, while higher frequencies more strongly stimulate the basilar membrane's base. Thus, electrodes of electrode array are located near the base of cochlea 232 are used to simulate high frequency sounds while electrodes closer to the apex are used to simulate lower frequency sounds. In some embodiments, only certain electrodes corresponding to certain frequency ranges are stimulated (e.g., with respect to a recipient who suffers from higher frequency hearing loss, the electrodes at the basilar membrane's base are stimulated, while those near the apex are not activated, and instead, the frequency allocation of the sound signal 203 is allocated to the acoustic hearing aid).

In at least some situations, the level and type of hearing loss of a person is often almost exclusively assessed utilizing pure tone audiometry which is presented in the form of an audiogram. By way of example only and not by way of limitation, such an audiogram can be utilized to determine which electrodes should be activated for stimulation and which frequency ranges should be reserved for acoustic stimulation by the acoustic hearing aid.

Audiograms are often utilized as the first step in fitting a hearing aid, with some subjective changes afterwards. Such pure tone audiometry to provide a person's audiogram typically consumes the time of a trained audiologist, and often requires at least one fitting session, and some specific audiometric equipment. For these reasons, these tests are not easily able to be carried out without a trained professional in an audiology clinic. In at least some exemplary embodiments according to the teaching detailed herein, by analyzing the speech of a person, one or more of the aforementioned "requirements" can be done away with. In this regard, people who have moderate to severe congenital deafness or early childhood deafness have, in at least some scenarios, significant changes to their speech production compared to their normal hearing peers. More subtle changes in speech production are reported in post-lingually deafened adults. Changes in speech production range from stressed and unstressed pitch variability, midpoints of voiceless fricatives, and plosive spectral slope. In at least some exemplary scenarios utilizing the teachings detailed herein, hearing loss has a number of known and measurable effects on speech production.

At least some exemplary embodiments according to the teachings detailed herein utilize advanced learning signal processing techniques, which are able to be trained to detect higher order, and non-linear, statistical properties of signals. An exemplary signal processing technique is the so called deep neural network (DNN). At least some exemplary embodiments utilize a DNN (or any other advanced learning signal processing technique) to analyze a person's speech to predict the likelihood that the person is suffering from hearing loss or from a change in his or her ability to hear. At least some exemplary embodiments entail training signal processing algorithms to detect subtle and/or not-so-subtle changes, and provide an estimate of the hearing loss of the recipient and specific information thereabouts. That is, some exemplary methods utilize learning algorithms such as DNNs or any other algorithm that can have utilitarian value where that would otherwise enable the teachings detailed herein to analyze a person's speech to predict hearing health outcomes such as their hearing loss, and/or appropriate fitting parameters and technologies for hearing devices.

A "neural network" is a specific type of machine learning system. Any disclosure herein of the species "neural network" constitutes a disclosure of the genus of a "machine learning system." While embodiments herein focus on the species of a neural network, it is noted that other embodiments can utilize other species of machine learning systems accordingly, any disclosure herein of a neural network constitutes a disclosure of any other species of machine learning system that can enable the teachings detailed herein and variations thereof. To be clear, at least some embodiments according to the teachings detailed herein are embodiments that have the ability to learn without being explicitly programmed. Accordingly, with respect to some embodiments, any disclosure herein of a device, system constitutes a disclosure of a device and/or system that has the ability to learn without being explicitly programmed, and any disclosure of a method constitutes actions that results in learning without being explicitly programmed for such.

Some of the specifics of the DNN utilized in some embodiments will be described below, including some exemplary processes to train such DNN. First, however, some of the exemplary methods of utilizing such a DNN (or any other algorithm that can have utilitarian value) will be described.

Figure 2:
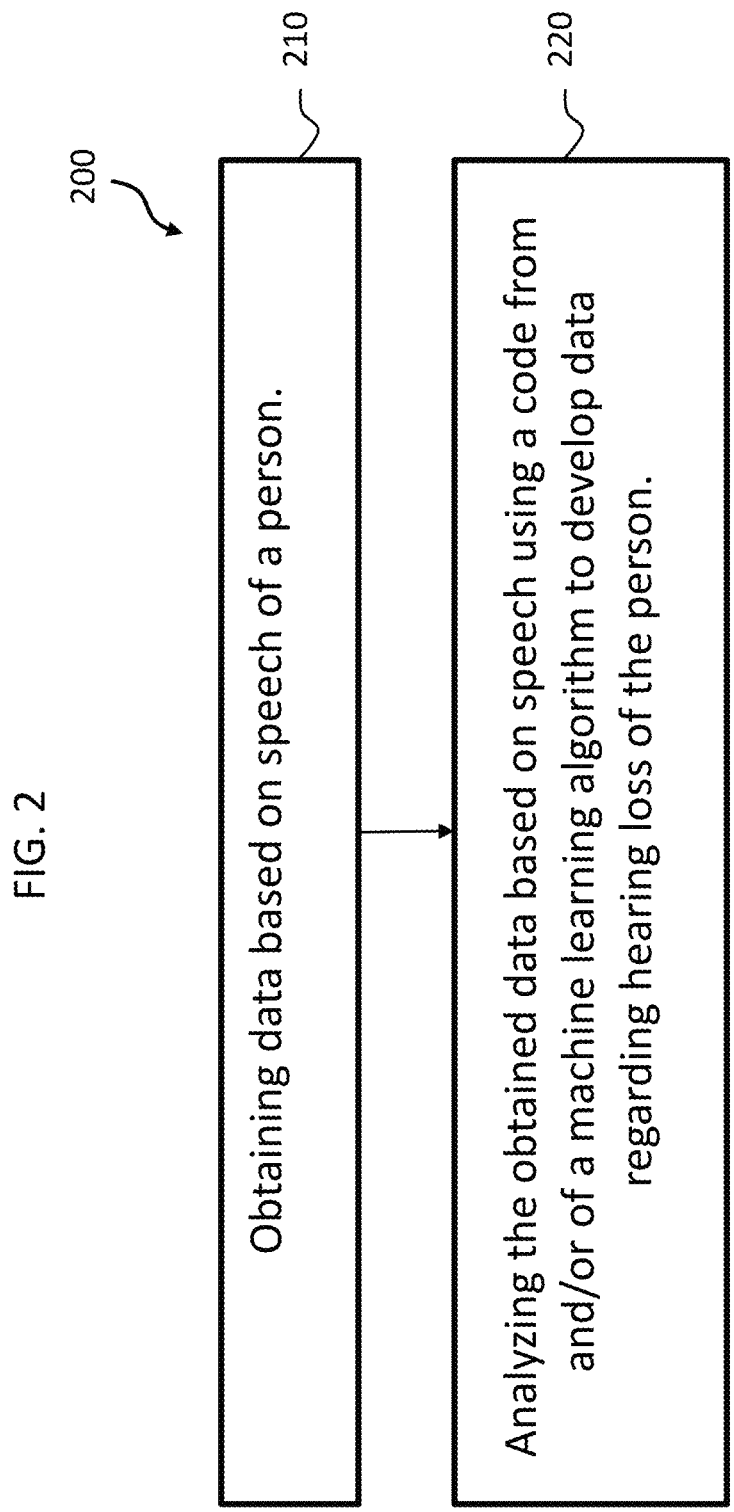
FIG. 2 depicts an exemplary flowchart for an exemplary method according to an exemplary embodiment.

FIG. 2 depicts an exemplary flowchart for an exemplary method, method 200, of utilizing a code of and/or from a machine learning algorithm, such as a DNN, according to an exemplary embodiment. Method 200 includes method action 210, which includes obtaining data based on speech of a person. In an exemplary embodiment, method action 210 is executed such that a user provides a speech sample as input. The speech could be any speech, such as reading from a book or newspaper, talking on a phone, or general dialogue. Any type of speech that can enable the teachings detailed herein can be utilized in at least some exemplary embodiments. In at least some exemplary embodiments, the speech sample can be a linguistically crafted piece of pose covering a wide linguistic range such as "the rainbow passage" or "comma gets a cure," by way of example only and not by way of limitation. In at least some exemplary embodiments, the speech sample can be recorded for processing by the DNN (or the code produced/from by the DNN).

That said, in an alternative embodiment, the action of obtaining data based on the speech of a person includes obtaining the data from an entity that obtained and/or analyzed the speech sample. That is, in an exemplary embodiment, to execute method action 210, the actor need not necessarily be the person who directly obtains the speech sample.

It is also noted that in at least some exemplary embodiments, method action 210 can be executed such that the person who is the subject of the method action is that a remote location from the entity obtaining the data based on the speech of the person. By way of example only and not by way of limitation, in an exemplary embodiment, the person speaking to a telephone, as noted above, and the telephone can transmit the person's speech to a remote facility, anywhere in the world in some embodiments, where the person's speech, which is representative of the speech of the person, is obtained upon receipt of the signal at least based on the signal generated by the person's telephone.

Method 200 further includes method action 220, which includes analyzing the obtained data based on speech utilizing a code of and/or from a machine learning algorithm to develop data regarding hearing loss of the person. Again, in an exemplary embodiment, the machine learning algorithm can be a DNN, and the code can correspond to a trained DNN and/or can be a code from the DNN (more on this below).

The developed data regarding the hearing loss could be a measure of the person's hearing health. This could be an estimate of the person's hearing loss in percentage or in dB attenuation or dB hearing loss. Any unit of measure for any indicia that can have utilitarian value can be utilized in at least some exemplary embodiments. In an exemplary embodiment, the developed data can correspond to an estimate of hearing loss at 500 Hz, 1 kHz, 2 kHz, and 4 kHz which can be utilized to create an audiogram, for example. In some exemplary embodiments, the developed data can correspond to the developed audiogram.

Figure 3:
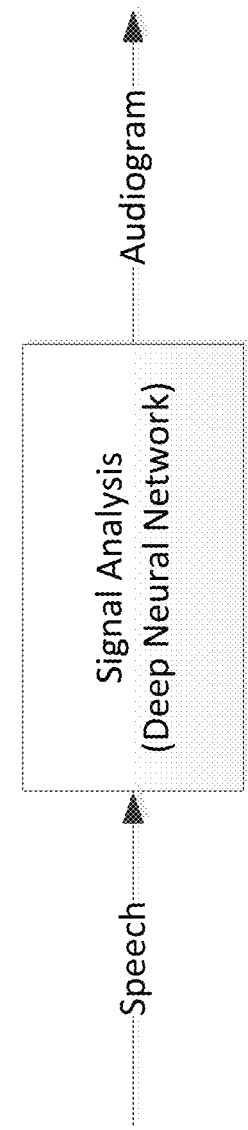
FIG. 3 depicts an exemplary conceptual schematic for a system according to an exemplary embodiment.

FIG. 3 depicts an exemplary conceptual schematic of an example of method 200, where speech is the input into a system that utilizes a trained DNN or some other trained learning algorithm (or the results thereof—the code of a machine learning algorithm as used herein corresponds to a trained learning algorithm as used in operational mode after training has ceased and code from a machine learning algorithm corresponds to a code that is developed as a result of training of the algorithm—again, this will be described in greater detail below), and the output is an audiogram.

It is noted that in at least some exemplary embodiments, any vocal input can be utilized with the system of FIG. 3. In at least some exemplary embodiments, the whole vocal range is analyzed to develop the resulting production. That said, in some alternate embodiments, only portions of the vocal range are analyzed to develop the resulting production.

It is noted that in at least some exemplary embodiments, it is not the speech signal that is provided directly to the learning algorithm. Instead, one or more feature extractions of the speech sample are calculated and provided as inputs to the learning algorithm. Such features can, in some embodiments, take in the whole speech sample, and provide a measure, or a set of measures from the speech sample. For example, overall loudness of the speech sample, the RMS, can be measures corresponding to a single feature. Alternatively, and/or in addition to this, loudness for one or more or any number of frequency bands can be determined, such as by calculating the power spectral density of the speech for, for example, 20 frequencies, and these 20 frequency specific powers are then provided to the algorithm. Alternatively, and/or in addition to this, other features can be extracted, such as other loudness measures, voicing measures such as pitch, jitter, pitch slope, pitch variability, etc., and/or articulatory features such as cepstrum, line spectral frequencies, and other analysis of the frequency spectrum.

Any data that is based on speech of a person can be utilized in at least some exemplary embodiments that can enable the teachings detailed herein can be utilized as input into the signal analysis algorithm, and thus any data that can enable the teachings detailed herein that is based on speech of a person can correspond to the data obtained in method action 210.

Figure 4:
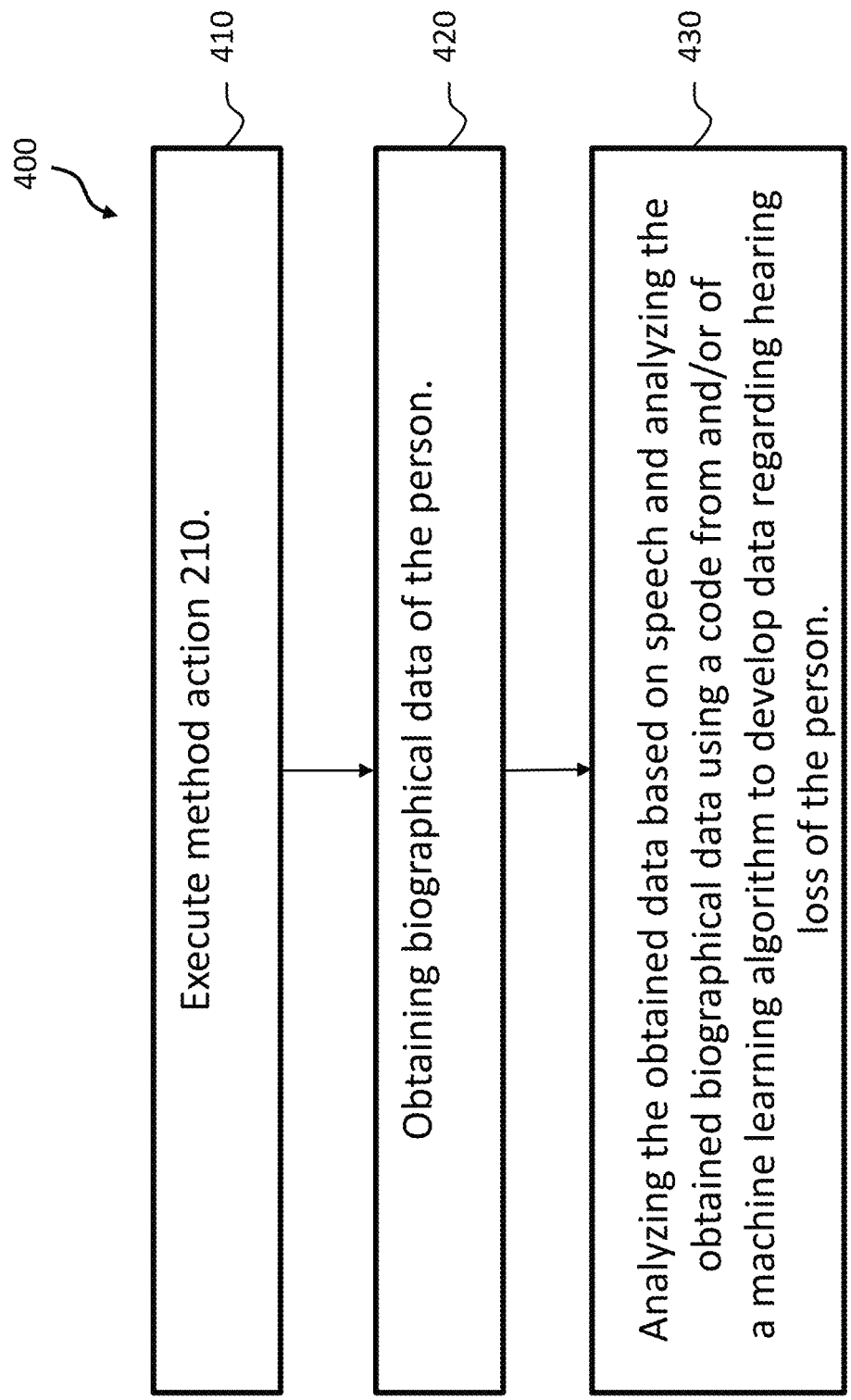
FIG. 4 depicts another exemplary flowchart for another exemplary method according to another exemplary embodiment.

FIG. 4 depicts another exemplary algorithm for another exemplary method, method 400, according to an exemplary embodiment. Method 400 includes method action 410, which includes executing method action numeral 210. Method 400 further includes method action 420, which includes obtaining biographical data of the person. By way of example only, such biographical data can be non-speech or non-hearing related data, such as age, gender, native language, intelligence, or some socioeconomic measure. Also, such biographical data can be the time since the person has lost his or her hearing or at least has had hearing problems, the time that the person had hearing prior to losing hearing (or starting to lose hearing), the number of years that the person was lingual prior to losing hearing, whether the person is lingual, etc. Any biographical data that can enable the teachings detailed herein and/or variations thereof can be utilized in some embodiments.

Method 400 also includes method action 430, which has parallels in some embodiments to method action 220, except that in addition to utilizing the obtained data based on speech, the method action 430 also utilizes the obtained biographical data in the analysis by the code to develop the data regarding the person's hearing loss.

To be clear, the data based on speech can be both "raw" speech and features extracted from that raw speech, or past speech or future speech. Indeed, in an exemplary embodiment, a speech therapist or the like or a trained hearing specialist trained to evaluate speech and make assumptions or estimates as to features of hearing loss can evaluate speech of the person subjectively and/or objectively and provides such data into the DNN. Also, the DNN can receive the raw speech. The DNN can use this data in combination to make the prediction as to the hearing loss of the recipient.

Figure 5:
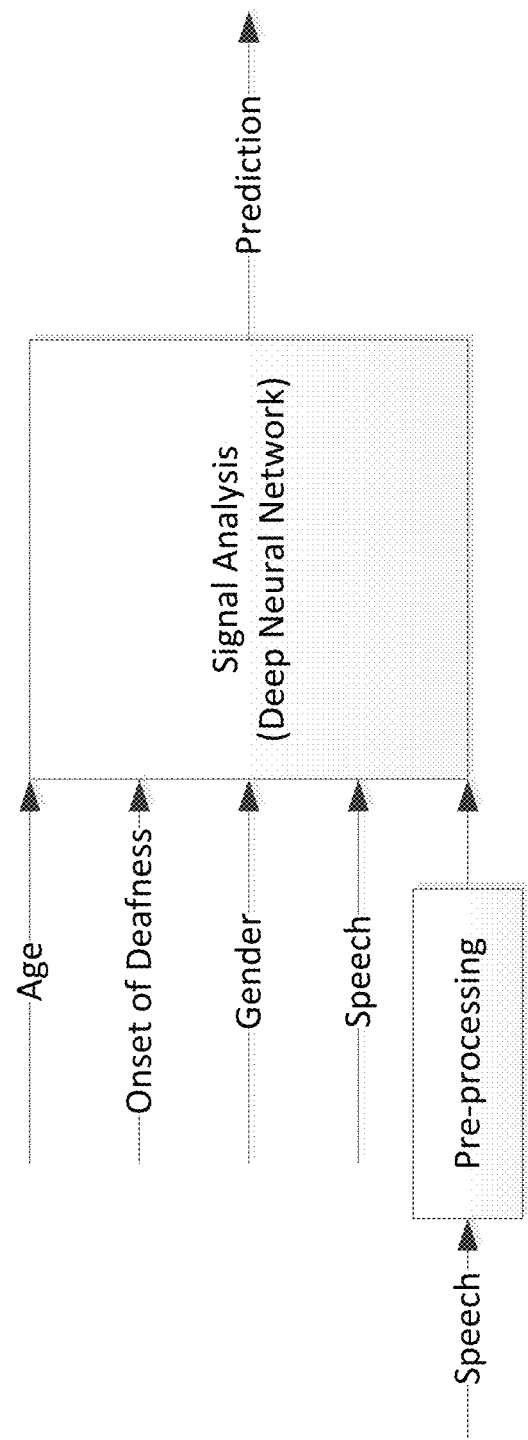
FIG. 5 depicts another exemplary conceptual schematic for another system according to an exemplary embodiment.

FIG. 5 presents a conceptual schematic of a DNN system depicting inputs therein and the output (prediction of hearing loss). As can be seen, in this exemplary embodiment, information such as age, data relating to the onset of deafness (how long ago, how long since birth, type, suddenness, etc.), the gender of the recipient, and the raw speech of the recipient is inputted into the DNN. Also, speech is "pre-processed," whether that be by a machine and/or by a human, and whether the speech that is pre-processed is the speech input into the DNN or whether that is different speech than the speech input into the DNN.

In an exemplary embodiment, the more independent information containing specific characteristics of the person provided to the learning model, the more accurate the prediction. To be clear, FIG. 5 depicts a system with a range of different inputs. Only one feature extraction input is shown (hearing loss prediction). However, in some alternate embodiments, there can be other feature extractions.

Note further that in some embodiments, there is no "raw speech" input into the DNN. Instead, it is all pre-processed data. Any data that can enable the DNN or other machine learning algorithm to operate can be utilized in at least some exemplary embodiments.

Figure 6:
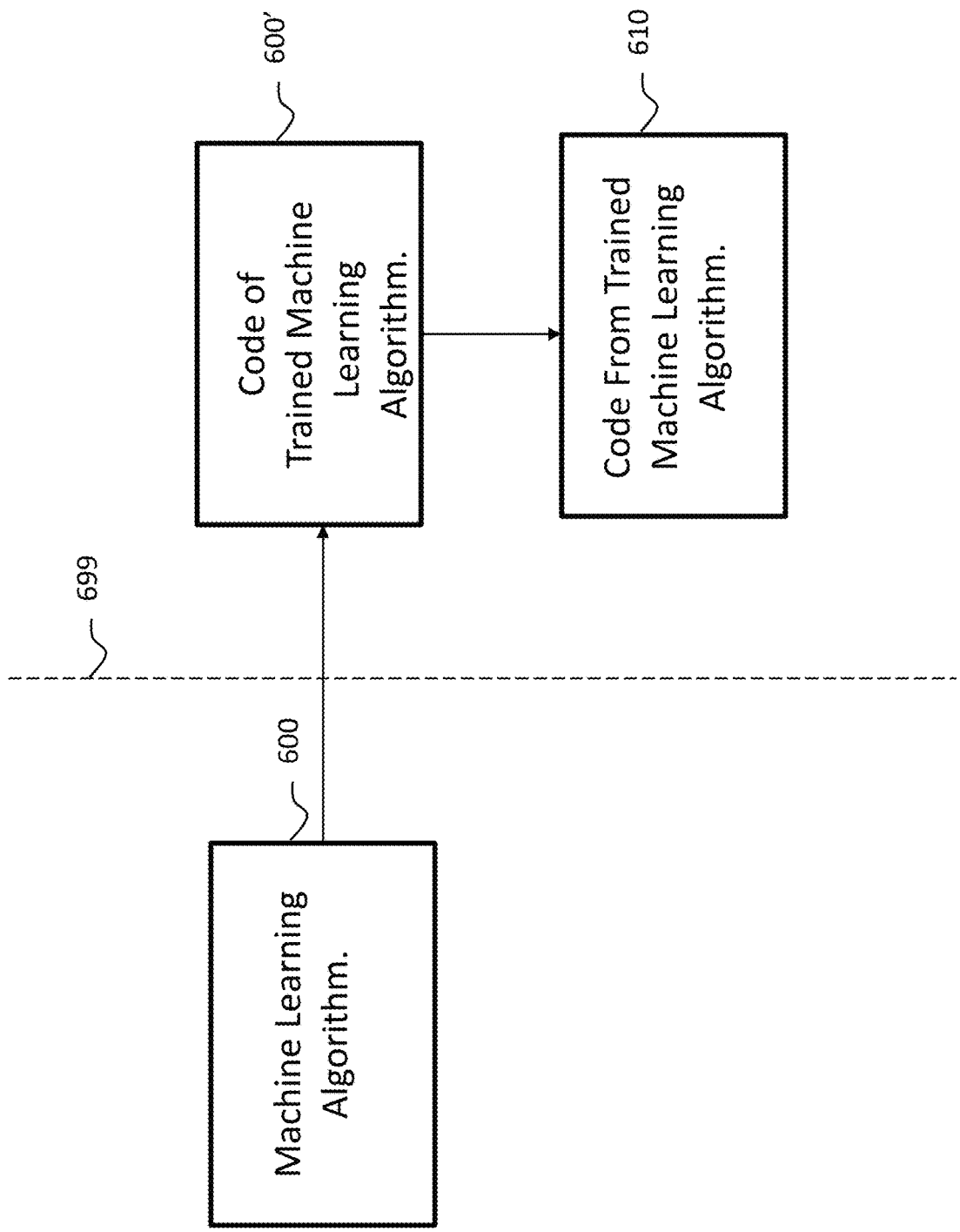
FIG. 6 depicts by way of conceptual functional schematic the progression of a machine learning algorithm as it is trained and an exemplary resulting offspring thereof.

Note that the embodiments above are utilized to predict hearing health measures. A range of hearing health or hearing benefit outputs can be, by way of example only and not by way of limitation:

An audiogram (few or many frequency measures)
A general level of deafness (a single overall level such as Pure Tone Average)
A measure of the benefits that could be provided by a hearing aid
A measure of the benefit that could be provided by a cochlear implant or other device
An assessment of the conductive and neural hearing loss components
A prediction of the etiology of hearing loss
A prediction of the age or length of profound hearing loss
A measure of the bilateral-ness of hearing loss As noted above, method 200 and method 400 utilize a code from a machine learning algorithm and/or a code of a machine learning algorithm. In this regard, the code can correspond to a trained neural network (the latter). That is, as will be detailed below, a neural network can be "fed" statistically significant amounts of data corresponding to the input of a system and the output of the system (linked to the input), and trained, such that the system can be used with only input, to develop output (after the system is trained). This neural network used to accomplish this later task is a "trained neural network." That said, in an alternate embodiment, the trained neural network can be utilized to provide (or extract therefrom) an algorithm that can be utilized separately from the trainable neural network. FIG. 6 depicts by way of conceptual schematic exemplary "paths" of obtaining code utilized in methods 200 and 400. With respect to the first path, the machine learning algorithm 600 starts off untrained, and then the machine learning algorithm is trained and "graduates" by symbolically crossing the line 699, or matures into a usable code 600'—code of trained machine learning algorithm. With respect to the second path, the code 610—the code from a trained machine learning algorithm—is the "offspring" of the trained machine learning algorithm 600' (or some variant thereof, or predecessor thereof), which could be considered a mutant offspring or a clone thereof. That is, with respect to the second path, in at least some exemplary embodiments, the features of the machine learning algorithm that enabled the machine learning algorithm to learn may not be utilized in the practice of method 200 or 400, and thus are not present in version 610. Instead, only the resulting product of the learning is used.

In an exemplary embodiment, the code from and/or of the machine learning algorithm utilizes non-heruistic processing to develop the data regarding hearing loss. In this regard, the system that is utilized to execute method 200 and/or 400 takes a speech signal in specifics or takes data in general relating to speech, and extracts fundamental signal(s) there from, and uses this to predict hearing loss. In at least some exemplary embodiments, the prediction beyond a general "hearing loss" number. By way of example only and not by way of limitation, the system utilizes algorithms beyond a first-order linear algorithm, and "looks" at more than a single extracted feature. Instead, the algorithm "looks" to a plurality of features. Moreover, the algorithm utilizes a higher order nonlinear statistical model, which self learns what feature(s) in the input is important to investigate. As noted above, in an exemplary embodiment, a DNN is utilized to achieve such. Indeed, in an exemplary embodiment, as a basis for implementing the teachings detailed herein, there is an underlying assumption that the features of speech and/or the other input into the system that enable the production of hearing loss to be made are too complex to otherwise specified, and the DNN is utilized in a manner without knowledge as to what exactly on which the algorithm is basing its prediction/at which the algorithm is looking to develop its prediction. Still further, in an exemplary embodiment, the output is a prediction of an audiogram, as opposed to general hearing loss data.

In at least some exemplary embodiments, the DNN is the resulting code used to make the prediction. In the training phase there are many training operations algorithms which are used, which are removed once the DNN is trained.

Note also, in at least some exemplary embodiments, the data developed in methods 200 and 400 regarding hearing loss of the person is developed without identified speech feature correlation to the hearing loss.

More generally, according to the teachings detailed herein, generic features are utilized, which features are associated with people being deaf or otherwise hard of hearing. No specific feature is utilized, or at least with respect to executing method 200 and/or 400 (or any of the other methods detailed herein), there is no specific feature of the speech and/or the biographic data that is looked at. Thus, a non-heuristic processing method is utilized. To be clear, in at least some embodiments, the specific features utilized to execute method 200 and/or 400 are not known (in some instances, they are not otherwise described), and one does not need to care as to what specific features are utilized. In at least some exemplary embodiments, a learning system is utilized which arbitrarily picks features within the input into the system in an attempt to "learn" how to predict hearing loss, and once the system learns how to predict hearing loss, it performs accordingly.

To be clear, in at least some exemplary embodiments, the trained algorithm is such that one cannot analyze the trained algorithm with the resulting code there from to identify what signal features or otherwise what input features are utilized to predict the hearing loss. This is as opposed to prior art predictive models that utilize frequency, for example, frequency features to predict hearing. In this regard, in the development of the system, the training of the algorithm, the system is allowed to find what is most important on its own based on statistically significant data provided thereto. In some embodiments, it is never known what the system has identified as important at the time that the systems training is complete. The system is permitted to work itself out to train itself and otherwise learn to predict hearing loss.

An exemplary scenario of training the system will now be detailed.

Any learning model that is available and can enable the teachings detailed herein can be utilized in at least some exemplary embodiments. As noted above, an exemplary model that can be utilized with voice analysis and other audio tasks is the Deep Neural Network (DNN). Again, other types of learning models can be utilized, but the following teachings will be focused on a DNN.

According to an exemplary embodiment of developing a learning model, a learning model type is selected and structured, and the features and other inputs (biographic, speech input, etc.) are decided upon and then the system is trained. It needs to be trained. In exemplary embodiments of training the system, a utilitarian amount of real data is compiled and provided to the system. In an exemplary embodiment, the real data comprises both sample speech (here, the single input, but in other embodiments, additional input, such as the biographic input, can be utilized) and the data one is trying to protect (here, the person's audiogram, for instance). Both the speech input and measure output (e.g., audiogram) are presented to the learning system (for one subject at a time). The learning system then changes its internal workings and calculations to make its own estimation closer to the actual person's hearing outcome. This internal updating of the model during the training phase can improve (and should improve) the system's ability to correctly predict the groups output. Subsequent individual subject's inputs and outputs are presented to the system to further refine the model. With training according to such a regime, the model's predictive accuracy is improved. In at least some exemplary embodiments, the larger and broader the training set, the more accurate the model becomes. An exemplary specific scenario is described below.

Thus, in this exemplary embodiment of the predictive model, both the input and the output is collected and provided to the model to train the model. In at least this exemplary embodiment, (i) the person's speech and (ii) a hearing health measure such as that person's audiogram are provided as input for the training. This is repeated for a statistically significant number of persons (e.g., 300 as used in the exemplary scenario below). In at least some exemplary embodiments, as will be described below, the input can also include or instead be the person's speech and that person's hearing aid fitting prescription/fit hearing aid settings (after 6 months of hearing aid acclimatization and fine tuning) for fitting output models (as opposed to hearing output models—again, an exemplary method of such will be described in greater detail below where the output is data for fitting a hearing prosthesis alternatively and/or in addition to the output being a prediction of the recipients ability to hear). In this last example, because it is not predicting a hard measure, but a more complex selection of fitting parameters and technologies, the learning model output can actually be more utilitarian on average than people's individual fittings previously received from hearing professionals. In an exemplary embodiment this can be because the system provides an "average" output of a range of professional's subjective fittings.

Still, focus for now will be on the scenario where the output of the trained learning system is a prediction of the subject's audiogram from that person's speech production. With respect to this scenario, the data collection for training and testing of the system can be as follows (by way of example only and not by way of limitation).

A subject (the subject used to train the system—again, this is training the system, not the use of a trained system as would be used to execute method 200 or 400) is instructed to speak for a statistically relevant amount of time (30 seconds, 1 minute, 90 seconds, 2 minutes, 3 minutes, 4 minutes, 5 minutes, etc., or any value or range of values therebetween in about one second increments, or more or less, reading from a book or from some form of prepared text. In an exemplary embodiment, the speech is recorded or otherwise captured by the sound capture device. In an exemplary embodiment, in addition to this, one or more demographic information data points are collected through a survey. All of this is linked to the subject. The subject is then tested with pure tone audiometry to obtain the subjects audiogram. This provides the inputs (speech and biographical data) and the output (audiogram).

In at least some exemplary embodiments, a statistically relevant number of subjects is utilized, and these subjects are representative of all the subjects that are intended to be the subject of method 200 and/or 400. In some embodiments, the data range of the subjects cover the following characteristics:

The data represents a general population (levels of hearing loss, age, gender, language, etc.)

The data contains members of each class (has multiple people in each segment)

The data contains a wide range of variance (noise effect via the utilization of multiple people in segment)

In some embodiments, with reference to the above, because the learning model of the system utilized in some embodiments is non-linear, and uses high order statistics, it is not directly known what feature(s) of the input are being used to make the prediction. Thus, in some embodiments, it is not possible to point to what in the input is the predictive feature. This differentiates from some prior methods of predicting hearing loss based on speech, where one or more specific features or to look towards in an effort to predict hearing loss. However, such can have utilitarian value with respect to enabling the investigation and use of a relatively large range of very complex features which are not able to be identified or even described.

In the case of a DNN, the size of the training can depend on the number of neurons in the input layer, hidden layer(s), and output layer. For instance, a system with three layers (input, hidden, and output) could have by way of example and not by limitation the following characteristics:
Input with a Total of 30 Neurons:
  12 loudness measures across the frequency spectrum
  12 spectral channels of modulation range
  3 channels of format estimates (F0, F1, F2)
  3 biographical inputs (length of hearing loss, age, gender)
Hidden Layer with a Total of 12 Neurons:
  The input layer neurons would have connections from each input and output neuron, as well as loop back and inter hidden layer connections.
Output Layer with a Total of 5 Neurons:
  A standard audiogram consisting of five spectral hearing loss levels at 500, 1000, 2000, 4000 and 8000 Hz.

Given this described system, a reasonable minimum number of training subject sets of data, spanning the subject spread for a simple feed forward DNN model could be:

$$Input*Hidden+Hidden*Output=30*12+12*5=420$$
subjects.

The example of the DNN model above can be trained with 420 people, but to test the accuracy of the developed model, additional data not used in training is used. In this case the data can also span the subject group. A number around 100 additional subjects could be suitable as long as there are multiple people in each segment. This data could be processed by the model, and the variance in the predicted outcome could be compared to actual audiogram of the verification subjects, and could be measured and used as the error (or prediction accuracy) of the model. After training and testing, the model would be well understood to operate in predicting people's outcomes by only receiving their speech sample.

It is noted that in at least some exemplary embodiments, larger test subject populations and/or smaller test subject populations can be utilized. In an exemplary embodiment, the test subject population can be 100, 125, 150, 175, 200, 250, 300, 350, 400, 450, 500, 550, 600, 650, 700, 750, 800, 850, or more test subjects. Any number of test subjects that can enable the teachings detailed herein can be utilized in at least some exemplary embodiments.

There are many packages now available to perform the process of training the model. Simplistically, the input measures are provided to the model. Then the outcome is estimated. This is compared to the subject's actual outcome, and an error value is calculated. Then the reverse process is performed using the actual subject's outcome and their scaled estimation error to propagate backwards through the model and adjust the weights between neurons, and improving its accuracy (hopefully). Then a new subject's data is applied to the updated mode, providing a (hopefully) improved estimate. This is simplistic, as there are a number of parameters apart from the weight between neurons which can be changed, but generally shows the typical error estimation and weight changing methods for tuning models according to an exemplary embodiment.

Figure 7:
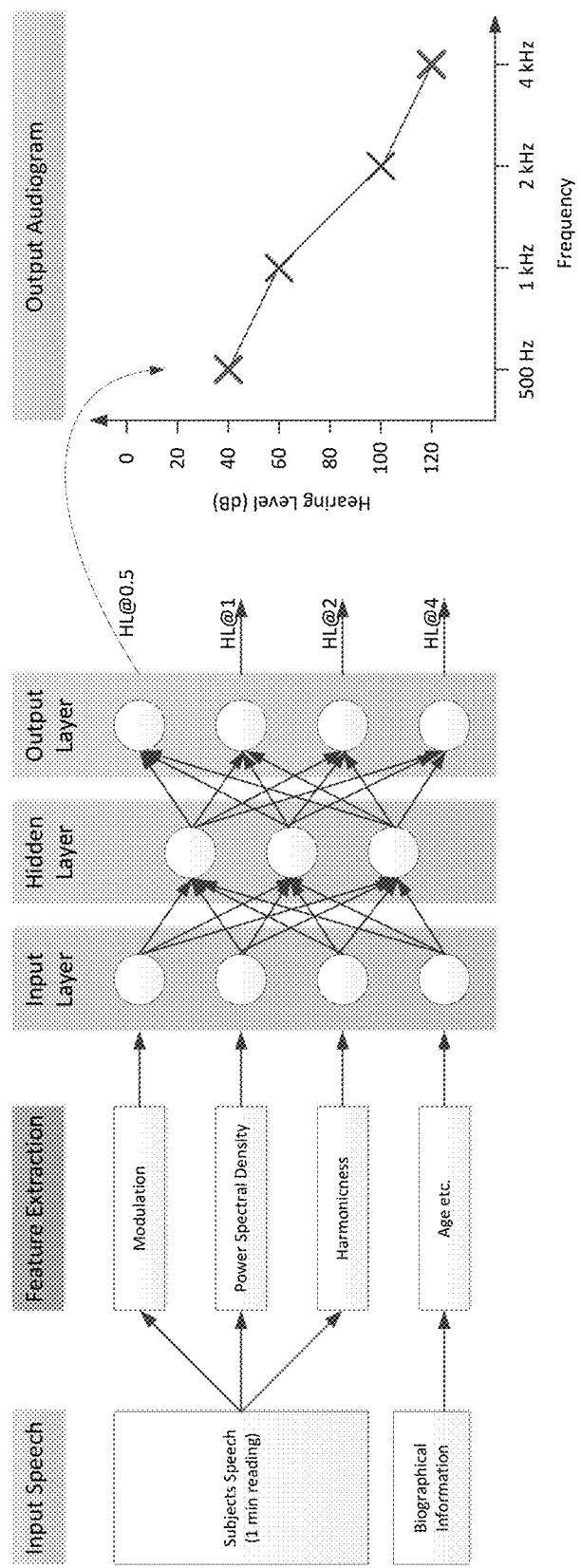
FIG. 7 depicts an exemplary schematic representing in graphical terms a method utilizing a neural network and the results thereof according to an exemplary embodiment.

FIG. 7 presents a conceptual schematic of a model of an exemplary complete system. A speech segment is processed to extract a number of features. These features as well as biographical information are provided as inputs to the learning model. The trained model then process these inputs to provide four outputs in this case (other outputs can exist). The outputs in this case are four pure tone thresholds at 500 Hz, 1 kHz, 2 kHz, and 4 kHz. These four outputs are then used to create an accurate prediction of the person's audiogram.

Figure 8:
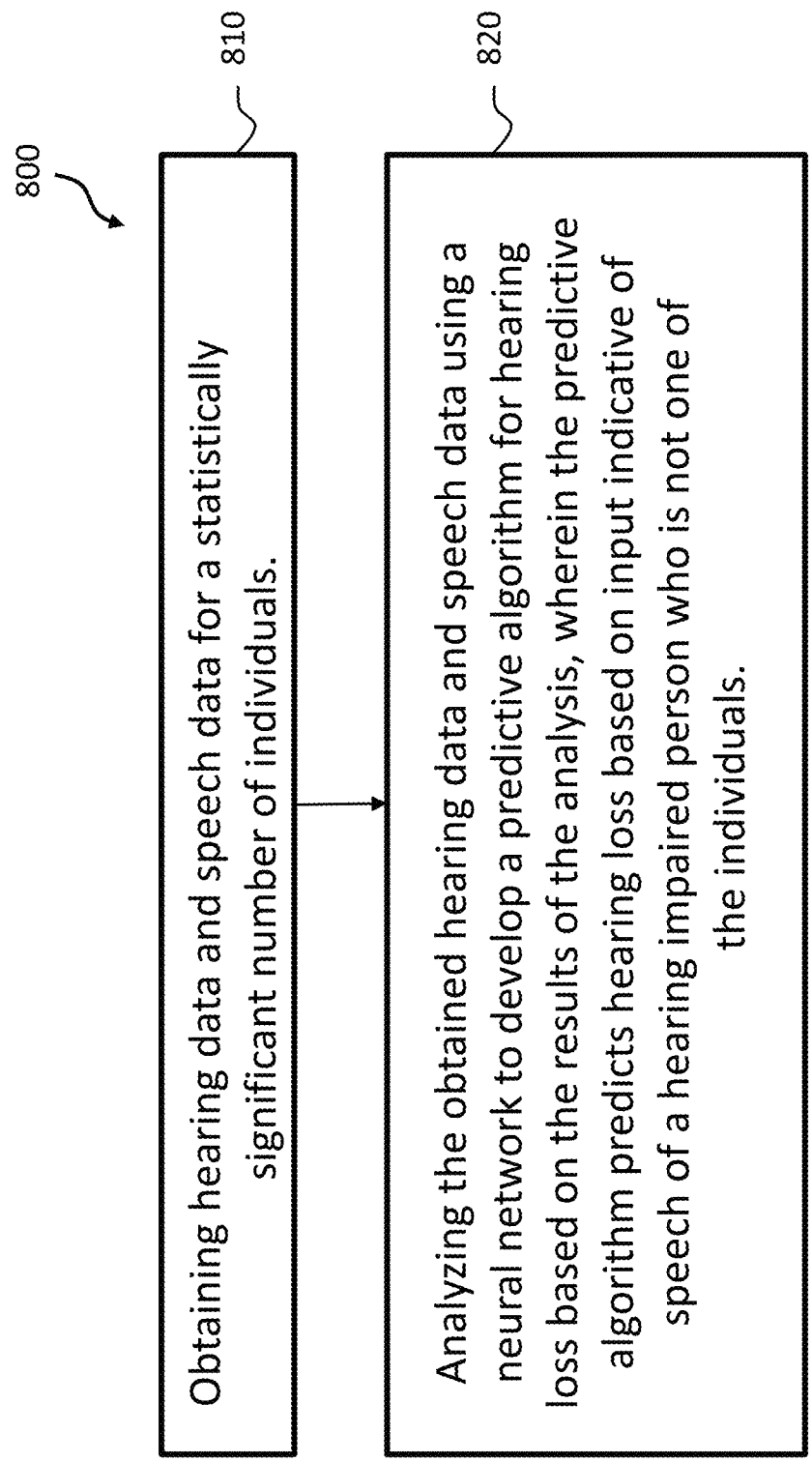
FIGS. 8-11 present exemplary flowchart for exemplary methods according to some exemplary embodiments.

In view of the above, FIG. 8 presents an exemplary flowchart for an exemplary method, method 800, of developing a predictive algorithm for hearing loss. In this exemplary embodiment, method 800 includes method action 810, which includes obtaining hearing data and speech data for a statistically significant number of individuals. This corresponds to, for example, the data of the 420 subjects detailed above by way of example only. Method 800 further includes method action 820, which includes analyzing the obtained hearing data and speech data using a neural network to develop a predictive algorithm for hearing loss based on the results of the analysis, wherein the predictive algorithm predicts hearing loss based on input indicative of speech of a hearing impaired person who is not one of the individuals. Method action 820 is executed utilizing, for example, the DNN detailed above, although in other embodiments, any other type of machine learning algorithm can be utilized in at least some exemplary embodiments. Consistent with the teachings detailed above, in an exemplary embodiment, the predictive algorithm is not focused on a specific speech feature. Instead, it utilizes a plurality of features that are unknown or otherwise generally represent a complex arrangement (if such can even be considered features in the traditional sense).

Still further, in some exemplary embodiments of method 800, again consistent with the teachings detailed above, the action of analyzing the obtained hearing data machine-trains a system that results in the developed predictive algorithm. Also, still with respect to method 800, in an exemplary embodiment, of the obtained hearing data and speech data, a portion thereof is used, in the neural network, for training and a portion thereof is used, in the neural network, for verification. Also, in this exemplary embodiment, the neural network develops the predictive algorithm by or transparently (sometimes, invisibly) identifying important features from the obtained hearing data and speech data. Also consistent with the teachings above, the predictive algorithm utilizes an unknowable number of features present in the speech data to predict hearing loss.

With respect to the unknown/transparent features, these can be features that are not related to a simple speech description. For instance, modulation is a term audiologists use to describe one aspect of speech. It may be that modulation is correlated with hearing loss. When unknowable and invisible/transparent are used to describe evaluating hearing loss in this regard, it is meant that that hearing loss is not typically (if at all) related to a feature, like modulation, which is known. It is not unknowable in technical terms, since the DNN is a description of the feature. This point is that this is not a simple audiological description of speech such as modulation, pitch, loudness, etc., or even a simple combination of these audiological descriptions, but the DNN will be looking at something which cannot be described simply by these terms, or a simple correlation or these terms.

Figure 9A:
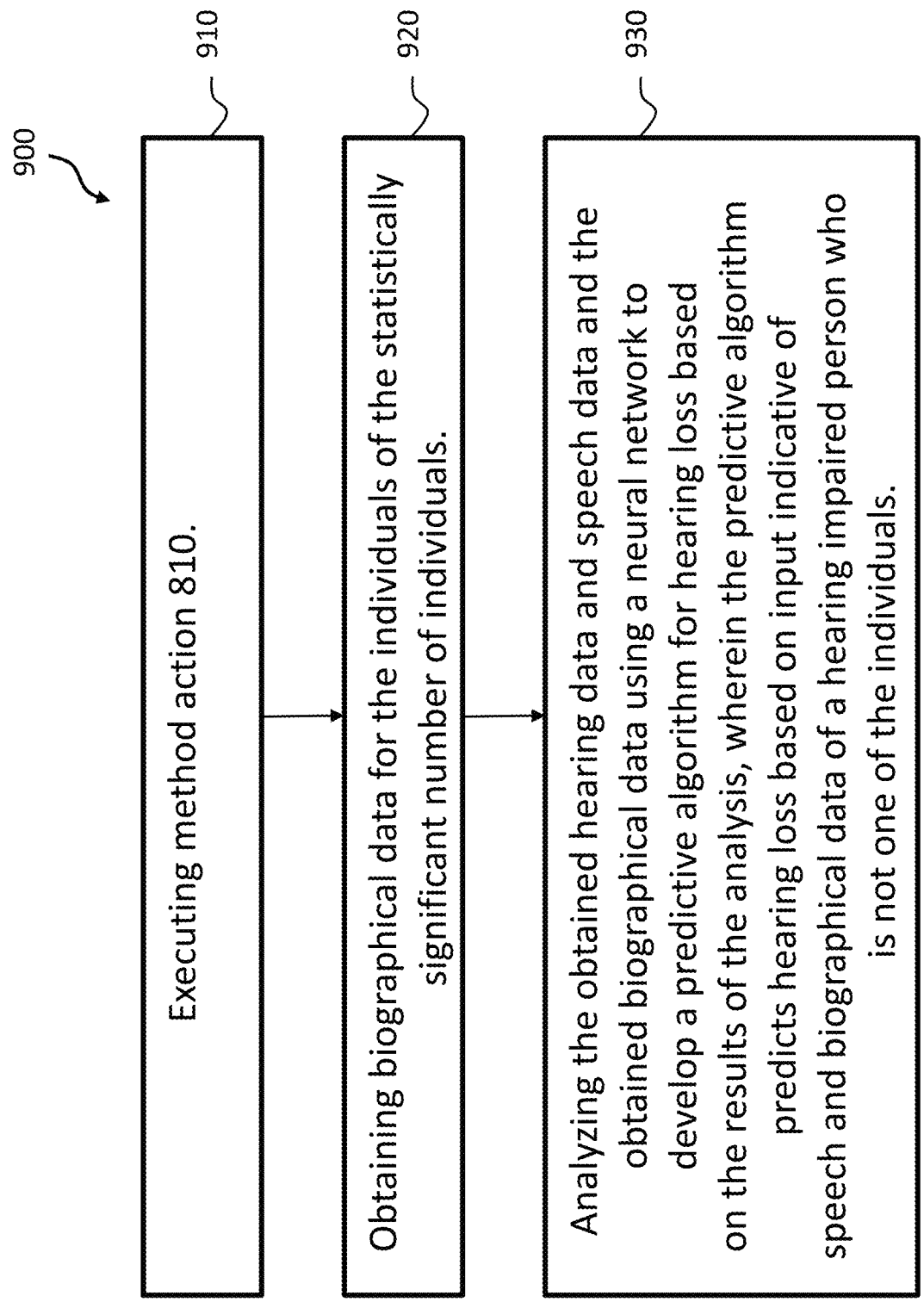

FIG. 9A presents an exemplary algorithm for an exemplary method, method 900, according to an exemplary embodiment. Method 900 includes method action 910, which includes executing method action 810. Method 900 further includes method action 920, which includes obtaining biographical data for the individuals of the statistically significant number of individuals of method action 910 (method action 810). Such can be executed in accordance with the teachings detailed above. Method 900 further includes method action 930, which generally parallels method action 820 detailed above, but includes, analyzing the obtained hearing data and speech data and the obtained biographical data using a neural network to develop a predictive algorithm for hearing loss based on the results of the analysis, wherein the predictive algorithm predicts hearing loss based on input indicative of speech and biographical data of a hearing impaired person who is not one of the individuals.

FIG. 9B depicts another exemplary method, method 940, according to an exemplary embodiment. The underlying idea behind method 940 is that the teachings utilized herein with respect to utilizing and train systems to predict hearing loss or the like can also be utilized to obtain data from a given subject to further train the DNN. In this regard, audiograms or the like can be developed or otherwise obtained in a traditional manner for a given subject of method 200 or 400. This audiogram or other data would not be utilized to predict the hearing loss per se, but instead would be utilized in a manner consistent with the training information detailed above (whether as a test subject for training or for model verification). Thus, in an exemplary embodiment, method 940 includes, in method action 950, executing method 800 and/or method 900 and then subsequently, in method action 960, executing method 200 and/or 400. In this regard, the code developed in method action 950 is utilized to execute method action 960. After method action 960 is executed, method action numeral 970 is executed, which includes obtaining data from the subject of method action 960, this data corresponding to the data of method actions 210 and/or 420. Utilizing this data, method 940 proceeds back to method action 950 and utilizes the data obtained in method action 970 to execute (re-execute) method 800 and/or method 900. It is noted that method action numeral 960 can instead correspond to obtaining data from the results of the execution of method 200 and/or 400. That is, instead of executing method 200 and/or 400, the actor who executes method 940 does not execute those method actions, but instead obtains the data from someone else, directly or indirectly, who is executed those method actions. FIG. 9C depicts such an exemplary alternative method of method 940, method 945, which includes method action 950 which corresponds to method action 950 detailed above. Method action numeral 980 corresponds to the action of obtaining data relating to a subject of the execution of method 200 and/or 400, where the code utilized to execute method 200 and/or 400 is the code that results from the method action 950. In an exemplary embodiment, the data corresponds to the data of method actions 210 and/or 420 plus additional data, such as by way of example only and not by way of limitation, in audiogram obtained in a traditional manner. Method 945 and then goes back to method action 950, which entails re-executing method 800 and/or method 900, but utilizing the data obtained in method action 980 to further train and/or validate the DNN, etc.

Briefly, it is noted that the neural networks or other machine learning algorithms utilized herein do not utilize correlation, or, in some embodiments, do not utilize simple correlation, but instead develop relationships. In this regard, the learning model is based on utilizing underlying relationships which may not be apparent or otherwise even identifiable in the greater scheme of things. In an exemplary embodiment, MatLAB, Buildo, etc., are utilized to develop the neural network. In at least some of the exemplary embodiments detailed herein, the resulting train system is one that is not focused on a specific speech feature, but instead is based on overall relationships present in the underlying statistically significant samples provided to the system during the learning process. The system itself works out the relationships, and there is no known correlation based on the features associated with the relationships worked out by the system.

The end result is a code which is agnostic to speech features. That is, the code of the trained neural network and/or the code from the trained neural network is such that one cannot identify what speech features are utilized by the code to develop the production (the output of the system). The resulting arrangement is a complex arrangement of an unknown number of features of speech that are utilized to predict the hearing loss of the subject. The code is written in the language of a neural network, and would be understood by one of ordinary skill in the art to be such, as differentiated from a code that utilized specific and known features. That is, in an exemplary embodiment, the code looks like a neural network.

Consistent with common neural networks, there are hidden layers, and the features of the hidden layer are utilized in the process to predict the hearing impediments of the subject.

The developed data of method 200 and 400, or, more accurately, variations thereof, could also be a less tangible measure, such as by way of example only and not by way of limitation, a factor or a range of factors as could be useful to determine a suitable hearing aid fitting. In this way, for example, the teachings detailed herein could bypass the intermediate process of using an audiogram to estimate a hearing aid fitting, and then have additional audiological tuning steps, and provide a final fitting estimate for the person (recipient). Some additional details of this are now described.

Figure 10:
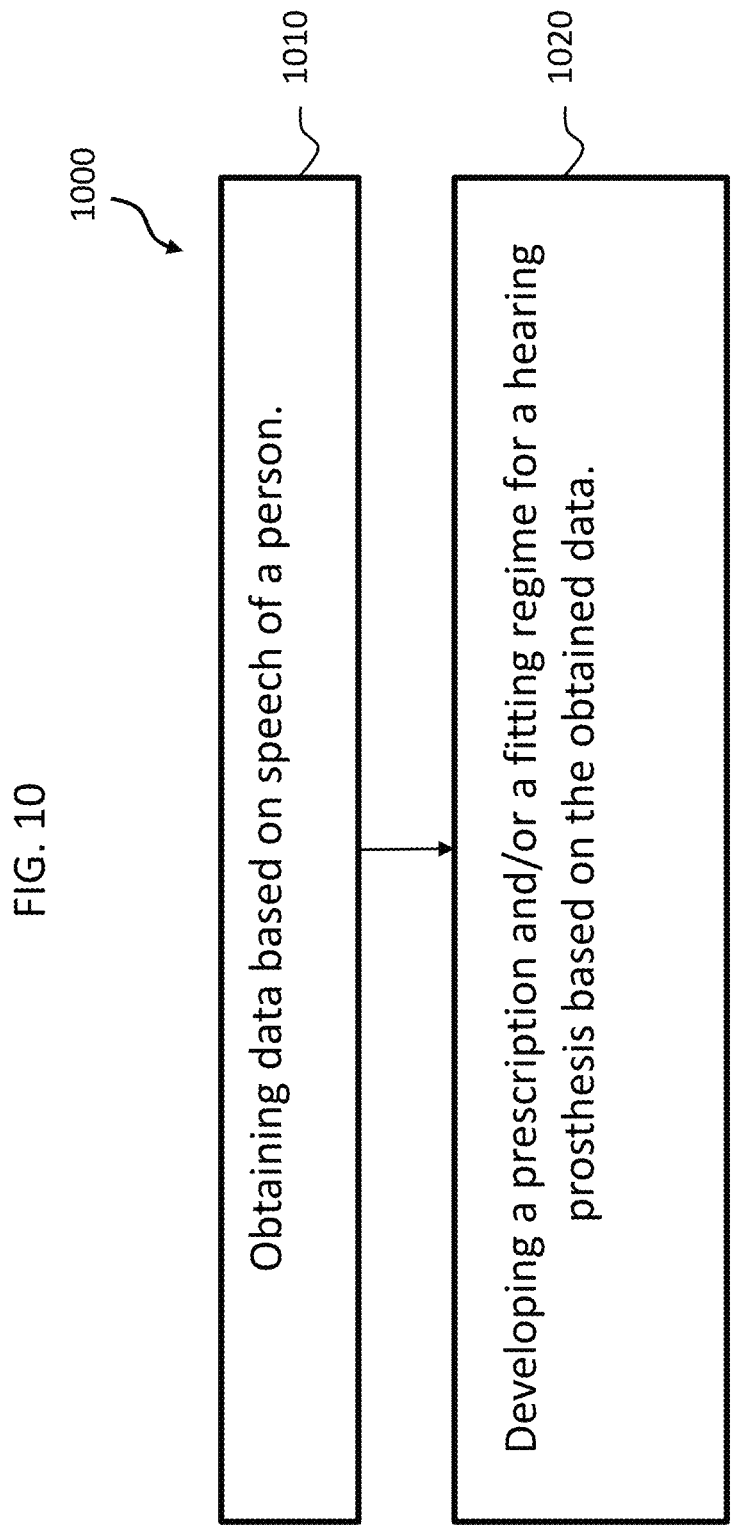

FIG. 10 depicts an exemplary flowchart for an exemplary method, method 1000, which includes method action 1010, which includes obtaining data based on speech of a person. In this regard, method action 1010 can correspond to method action 210 and/or 410 detailed above. Indeed, in an exemplary embodiment, method 1000 can be an offshoot of method 200 and/or 400 detailed above. That is, an exemplary method can start off with method 210, and can then branch off by executing the remaining actions of method 200 and 400 on the one hand, and the following actions of method 1000 on the other hand. With respect to the following actions, in an exemplary embodiment, method 1000 further includes method action 1020, which includes developing a prescription and/or a fitting regime for a hearing prosthesis based on the obtained data obtained in method action 1010. As noted above, in an exemplary embodiment, method 1000 completely skips the results of method 200 and 400. Instead, the result is output corresponding to how the hearing prosthesis should be fitted to the recipient. Also, consistent with the teachings detailed above that utilize a neural network, in an exemplary embodiment, the prescription can be developed based on relationships as opposed to correlations between speech and hearing loss. That said, it is noted that in at least some exemplary embodiments, method 1000 is executed without utilizing a neural network or otherwise some form of machine learning algorithm or code based thereon. Still, in at least some exemplary embodiments, method 1000 is executed by utilizing a code written in the language of a neural network to develop the prescription and/or fitting regime.

Consistent with utilization of the method 1000 for fitting a conventional hearing aid, in an exemplary embodiment, the prescription and/or fitting regime is a gain model. In this regard, an exemplary embodiment, this gain model can be applied to the hearing prostheses to determine what gain should be applied at least for certain frequencies. Note also that such can be applicable to other types of hearing prostheses, such as by way of example only and not by way of limitation, cochlear implants, middle ear implants, bone conduction devices etc. Any prosthesis to which the teachings detailed herein can be applied can be utilized in at least some exemplary embodiments.

It is further noted that in at least some exemplary embodiments, the results of method 1000 (or method 1100, as will be described below) are utilized via input via the user interface 280 and an external processor 282 of FIG. 1A to fit the hearing prosthesis. In this regard, an exemplary embodiment includes utilizing the results of method 1000 (or method 1100), or any of the other applicable methods detailed herein, to program or fit the hearing prosthesis utilizing the arrangement of FIG. 1A.

Figure 11:
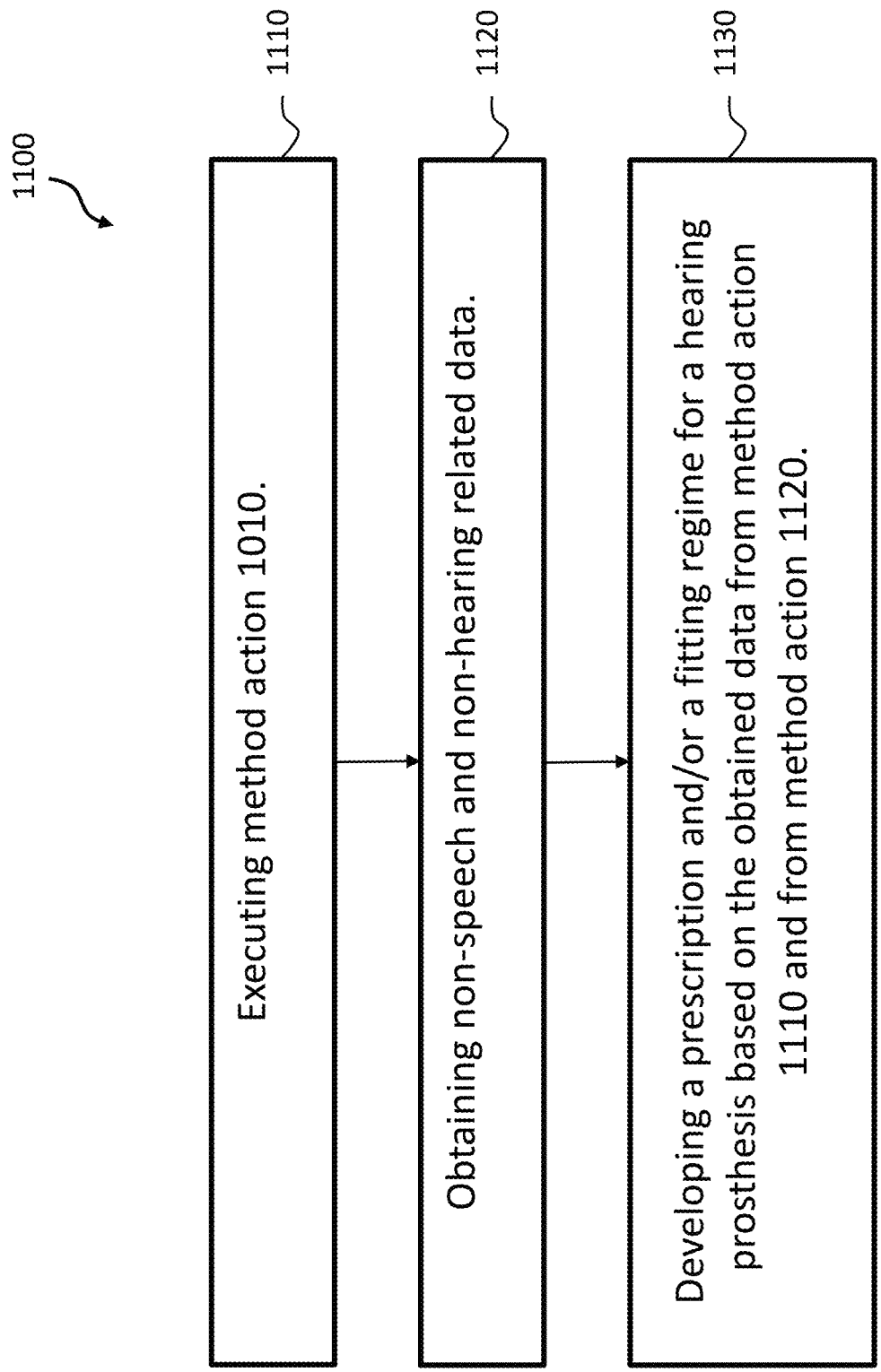

FIG. 11 represents an exemplary flowchart for an exemplary method, method 1100, which generally parallels method 1000 above, but which also utilizes non-speech and non-hearing related data. In this regard, method 1100 includes method 1110, which entails executing method action 1010. Method 1100 also includes method action 1120, which includes obtaining non-speech and non-hearing related data. In an exemplary embodiment, this can correspond to the biographic information detailed above. Any non-speech and/or non-hearing related data that can enable the teachings detailed herein in general, and can enable method 1100 in particular, can be utilized in at least some exemplary embodiments. Method 1100 further includes method action 1130 which includes developing a prescription and/or a fitting regime for the hearing prostheses based on the obtained data for method action 1110 and from method action 1120. In this regard, method 1100 generally parallels method 400 detailed above which utilizes the biographic data. It is noted that method 1000 and method 1100 can be executed so as to bypass the development of an audiogram or otherwise the developments of data relating to the hearing deficiencies of the subject. Instead, in an exemplary embodiment, the action of developing a prescription and/or the fitting regime is executed directly from the obtained data obtained in method actions 1110 and/or 1120. This is as opposed to executing such indirectly from the obtained data (e.g., via the use of an intervening audiogram to develop the prescription and/or fitting regime).

Thus, an exemplary output of an exemplary system (utilizing code written in the language of a machine learning algorithm or otherwise) can use any of the measures detailed herein to determine a hearing prosthesis's fitting, and to determine such fitting directly. The fitting is the specific parameters and technologies to be used by the hearing prosthesis during use for a particular recipient. For instance, a number of measures could be used to determine the gain system settings as noted above, but also some of the other signal processing technology settings. Also, suitable automation settings can be utilized in some exemplary embodiments. In this way, a set of hearing aid parameters could be determined directly from a recipient's (or future recipient's) input. This can comprise two or more separate models, where the internal measures of hearing can be provided to a second fitting model. Or such can comprise a single learning model which has no internal knowledge of the measures typically used in predicting fitting parameters.

Thus, in contrast to some prior methods of fitting a hearing prosthesis, instead of obtaining an audiogram and, based on the audiogram, developing a fitting regime/prescription for a hearing prosthesis, the teachings detailed herein can skip the acquisition of an audiogram, or even the development of specific data indicative of a person's hearing loss, and instead, a prescription/fitting regime can be directly developed from the inputs. While the teachings detailed herein focus on some embodiments of the utilization of a learning model, in other embodiments, a learning model is not utilized. Still, in at least some exemplary embodiments, a learning model is utilized to predict a fitting regime or prescription based on the input in a manner analogous to or otherwise corresponding to that which was applied in developing the systems to protect hearing loss. In this regard, in an exemplary embodiment, any of the teachings detailed herein with respect to developing the system to protect hearing loss and/or the utilization of such system to predict hearing loss also corresponds to teachings that are applicable to the development of a system to predict a fitting regime and/or a prescription and/or the utilization of such a system to protect the fitting regime and/or prescription.

With respect to some specifics of a predicted fitting regime and/or prescription, in an exemplary embodiment, the results of methods 1000 and/or 1100 or the other methods detailed herein is a NAL prescription in whole or in part. In an exemplary embodiment, the prescription can be for the conventional hearing aid and/or for a cochlear implant, or any other hearing prosthesis. In an exemplary embodiment, such as where the fitting regime is utilized for a cochlear implant, a noise reduction fitting regime and/or a gain fitting regime can be the result of methods 1000 and 1100. Still further, the result can be a predicted gain model for the hearing prostheses. Note also that as will be described in greater detail below, in an exemplary embodiment, the prescription is eliminated in its entirety. Instead, the result is a fitting regime for a hearing prosthesis that is directly applied to the hearing prosthesis (e.g., the fitting regime constitutes programming for the hearing prostheses that when applied to the hearing prostheses, the hearing prostheses configures itself to operate accordingly—this can be entirely transparent to the recipient and/or the healthcare professional). In such embodiments that apply such, along with the embodiments that apply such and also skip the development of the audiogram, streamlining of the fitting process can be achieved.

In an exemplary embodiment, the results of methods 1000 and/or 1100 are a prescription and/or a fitting regime that enables the hearing prosthesis of U.S. Pat. No. 4,803,732 to Dillon (issued Feb. 7, 1989) and/or the hearing prosthesis of U.S. Pat. No. 5,278,912 to Waldhauer (issued Jan. 11, 1994), to be fitted or adjusted per the prescription. In this regard, in an exemplary embodiment, the resulting prescription and/or fitting regime includes data for adjusting one or more features of the respective hearing prostheses of these patent documents. Also, the results of method 1000 and/or 1100 can be a prescription and/or a fitting regime that provides for sound compression/signal compression for the pertinent subject. By way of example only and not by way of limitation, the results of method 1000 and/or 1100 can enable the input controlled compression to be utilitarian or otherwise controlled for a specific recipient. Also by way of example, the results of method 1000 and/or 1100 can be that which enables or otherwise identifies the utilitarian fitting compression for a given hearing prostheses for that recipient.

To be clear, in some exemplary embodiments, the results of method 1000 and/or 1100 and/or the results of methods 200 and 400 can be used to develop hearing prosthesis data such as hearing prosthesis frequency specific gains, a hearing prosthesis gain system, the selection of suitable processing technologies or the level (strength) of a range of hearing technologies (e.g., noise reduction, directional microphone application, and the weighting of the given technology relative to one another (if used in combination) etc.) etc.

Also, in an exemplary embodiment, the unilateral and/or bilateral amplifications can be determined as a result of methods 1000 and/or 1100. Of course, in some embodiments, the results can be a prescription of an amplification regime for a given hearing prosthesis.

In view of the above, in an exemplary embodiment, the results of method 1000 and/or 1100 can be the settings of a given hearing prosthesis/programming of a given hearing prosthesis and/or data for setting a given hearing prosthesis or programming a given hearing prosthesis with respect to a gain model, feedback management, frequency compression, noise reduction, etc., for a given recipient or subject based on the data of method actions 1010 and/or 1120.

Figure 12:
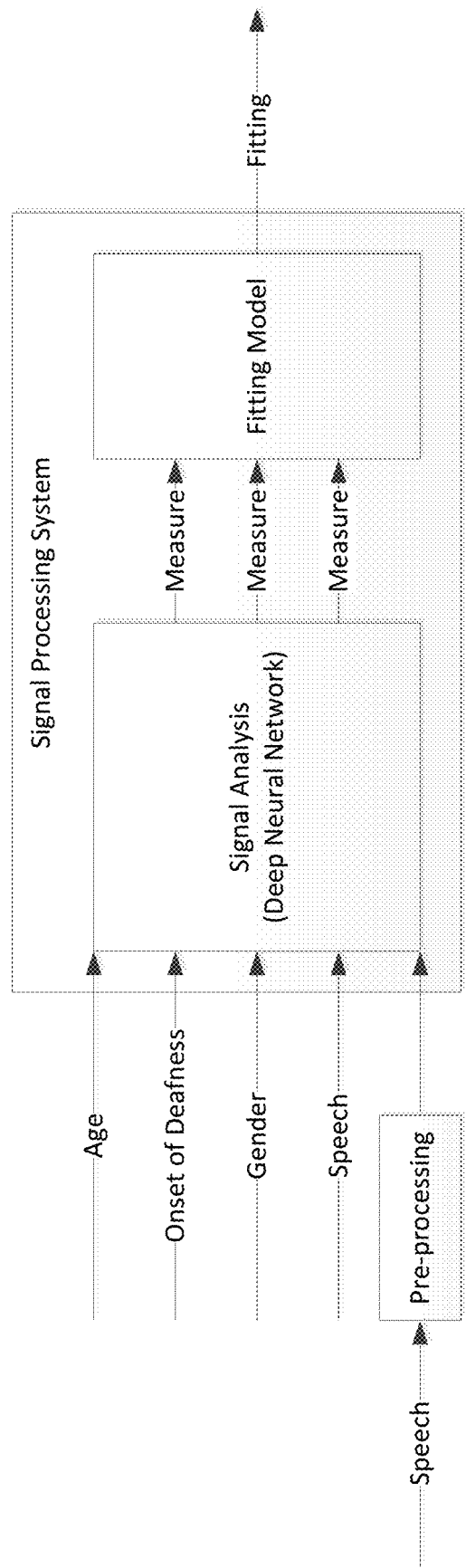
FIG. 12 depicts an exemplary schematic conceptually illustrating a system according to an exemplary embodiment.

FIG. 12 presents an exemplary conceptual schematic according to such an exemplary embodiment utilized for fitting/prescription development. More specifically, FIG. 12 presents an exemplary learning algorithm which has two stages: the first stage is to predict the hearing health outcome and measure such as an audiogram. The second stage is to determine the most suitable hearing aid fitting/prescription.

Thus, in view of the above, utilizing speech input data, whether in raw format or in a preprocessed format, or in combination, along with non-speech and/or non-hearing related data, such as age, gender, etc., the teachings utilize herein can be applied to predict or otherwise develop data relating to a hearing loss of a subject and/or to predict or otherwise develop data relating to fitting of a hearing prosthesis/the development of a prescription for a hearing prosthesis. As noted above, in an exemplary embodiment, separate methods can be practiced where the output is respectively data relating to hearing loss and data relating to how to program or otherwise fit a given hearing prostheses, whereas in some exemplary embodiments, the methods can be practiced in combination with the output is both the hearing loss and the programming information. Still further, as noted above, in some embodiments, the hearing loss data can be skipped in its entirety, and, in some embodiments, the output can be entirely directed towards programming information/fitting information.

The below is a chart presenting high-level concepts of the types of predictions that can be made utilizing the teachings detailed herein and/or variations thereof, along with exemplary input and output for such predictions. It is also noted that the input and output also corresponds to the input when developing a predictive model for such predictions:

| Description | Input | Output |
| --- | --- | --- |
| General hearing loss prediction | Speech (from a paragraph) | PTA (average of HL at 0.5, 1, 2 and 4 kHz) |
| Audiogram prediction | Speech, biographical information | Audiogram |
| Fitting of gain system (HA, or CI) | Speech, biographical information | Gains, knee points and time constants |
| Fitting of technology use (HA, or CI) | Speech, biographical information | Settings for dir. mics, NR systems |
| Predicting Benefit in speech understanding | Speech, biographical information | Words correct in quiet or in noise |
| Predicting Benefit in quality of life measure | Speech, biographical information | SSQ, QoL survey results |
| Conductive vs sensorineural levels | Speech, biographical information | Level of each, or proportion of each |
| Hearing loss etiology | Speech, biographical information, biometric | Etiology of hearing loss |
| Determine the length of hearing loss | Speech, biographical information | Number of years of mild and severe hearing loss |
| Bilateral hearing | Speech, biographical information | Difference in hearing loss between ears |

An exemplary data flow used to create a predictive configuration model that is usable in an automatic prosthesis configuration program and/or automatic hearing impairment data identification will now be described. In this regard, in an exemplary embodiment, the teachings detailed herein can be utilized or otherwise can be modified to be utilized in a situation where a recipient is wearing a hearing aid (a conventional hearing aid) and/or a cochlear implant (or other type of hearing prosthesis) so as to detect through the recipient speech if the recipient's hearing prostheses is not restoring his or her hearing to a desired/optimal level. By way of example, the recipient wears the hearing prostheses during testing, and the teachings detailed herein and/or variations thereof are utilized to predict, from the recipient speech, changes that could be implemented to the hearing prostheses so as to improve hearing. By way of example only and not by way of limitation, a change to the map or a change to the processing regime, etc. It is further noted that in at least some exemplary embodiments, the data that is utilized to train the machine learning systems detailed herein can be developed utilizing a statistically significant population that has a hearing aid and/or a cochlear implant, etc.

Note that in some embodiments, the teachings detailed herein are implemented in a three stage process. First, the teachings detailed herein are implemented with respect to people who do not have a hearing prosthesis. These teachings are utilized to determine the suitability or otherwise utilitarian value with respect to having a given recipient utilize a conventional hearing aid and/or with respect to fitting a conventional hearing aid there to. Such can also be the case with respect to determining the suitability or otherwise utilitarian value with respect to having a given recipient utilize a bone conduction device, which device can be utilized with recipients who are hard of hearing, but still hear (analogous to recipients who have suitability for a conventional hearing aid but who do not have sufficient hearing impairment to warrant a cochlear implant). Next, the teachings detailed herein are implemented with respect to people who have a conventional hearing aids (and/or, in the exemplary scenario, bone conduction devices), to determine the suitability or otherwise utilitarian value with respect to having a given recipient utilize a cochlear implant, or otherwise with respect to fitting such cochlear implant.

In this example, a predictive configuration model is based on data mining principles created from large sets of empirical data. In this example, input training data is used to build the predictive configuration model and can include many instances of individual sets of matching data, which have been empirically obtained from a large number of cochlear implant recipients, conventional hearing aid recipients, bone conduction device recipients, middle ear recipients, etc. These individual sets of matching data can include objective physical measurements, training configuration variables, and stimulation parameters.

More specifically in this example, objective physical measurements can include any one or more of the characteristics earlier identified. Similarly, the training configuration variables can include, but are not limited to subjectively determined values. A machine learning algorithm then undergoes a "training" process to determine one or more values related to fitting the hearing prosthesis, a prescription for a hearing prosthesis and/or related to hearing impairments of the recipient.

It is noted that in an exemplary embodiment, the input data for any of the methods detailed herein can be obtained via a dedicated speech testing regime, which can include sitting in front of a personal computer or tablet or the like, or can include the subject speaking into a telephone and/or inputting non-speech data/biographic data, into a computer. Such can be executed in so called "point of care" sessions in the clinical setting and/or in so-called "remote care" settings, at home or remote from a central care provider. Thus, in an exemplary embodiment, the raw speech upon which the various methods detailed herein are based can be captured at a clinic and/or remotely, using a hearing prosthesis or other devices (phone, dedicated microphone, etc.), which can capture the sound and convey it to the system that is undergoing training and/or the trained system/system using the code from the train system. Again, additional data can be collected at the point where the raw speech is captured or subsequently which additional data can be by way of example only and not by way of limitation, patient specific information such as age, etiology, genetic information, and information about any hearing prosthesis being used.

The smart phone or other remote component can analyze the data stream thereto to extract data and/or can act as a medium to pass the data stream thereto to the cloud for cloud computing. That is, the smart phone or other remote device passes the collected information from the remote device to the cloud.

The system includes a link from the cloud to a clinic to pass the information uploaded to the cloud to the clinic, where the information can be analyzed. Another exemplary system includes a smart device, such as a smart phone or tablet, etc., that includes a sound capture device, that is running a purpose built application to implement some of the teachings detailed herein. In this exemplary system, the hearing prosthesis is bypassed or otherwise not utilized. Indeed, in this exemplary system, a hearing prosthesis may not be utilized at all. That is, in an exemplary embodiment, the person that is speaking is not a recipient of the hearing prosthesis, but instead a subject who could be hard of hearing. In an exemplary embodiment, the smart device can be configured to present a series of words for the recipient to repeat, which words are words that have been preselected for the purpose of identifying hearing attributes based on the speech of hearer/subject. In this regard, the hearer/subject vocalizes the visual signals that are presented on the smart device (e.g., speaks the words displayed on the smart device). The subject's speech is then picked up by the smart device's microphone. The smart device either uploads the speech to the cloud or otherwise analyzes the speech and uploads the analysis and/or raw speech or other data to the cloud. Alternatively, the smart device can analyze the speech autonomously according to the teachings detailed herein. In an exemplary embodiment, the cloud stores the results of the tests across all subjects, and data can be sent to the relevant clinic for use in the methods detailed herein.

Figure 13:
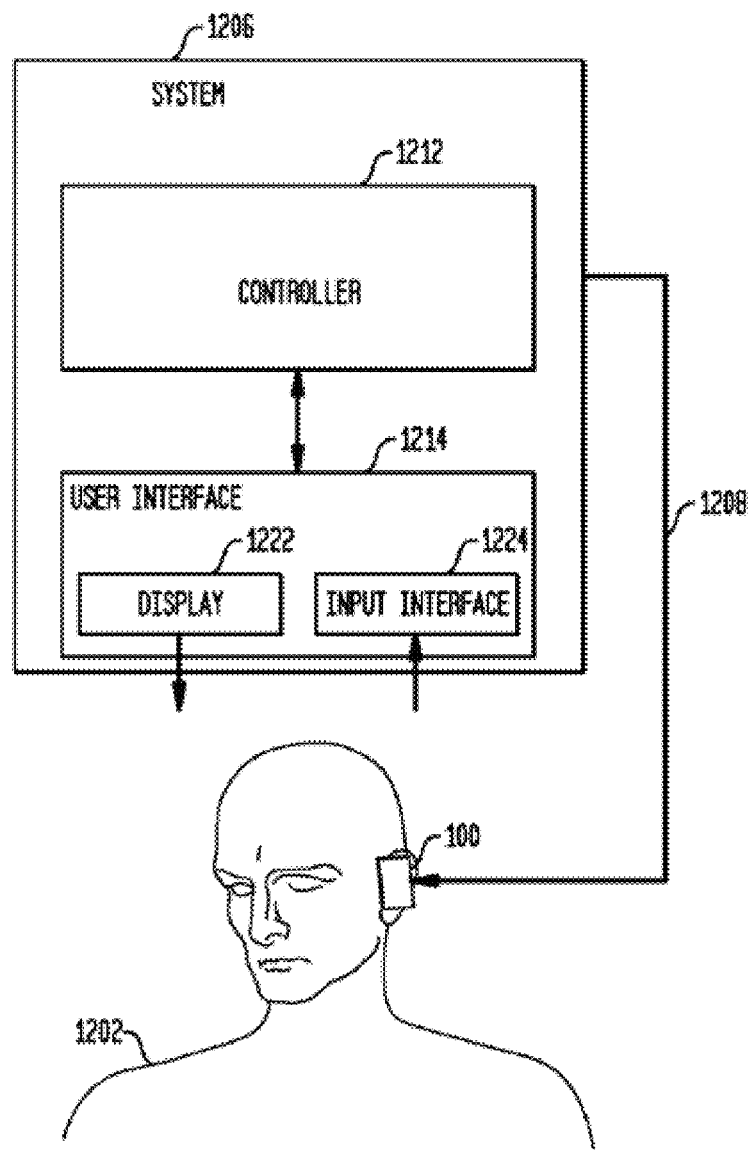
FIG. 13 depicts a schematic functionally representing an exemplary system.

It is noted that there can be a wide variety of data (input data) collection techniques and/or acquisition techniques, whether the data be utilized for the methods detailed herein with respect to developing fitting data for a prosthesis or for ascertaining a hearing impairment of a subject, or for developing the data to train the learning algorithm's detailed herein. Such can entail the utilization of a smart phone, a dedicated microphone, a personal computer, a landline phone, etc. In this regard, in an exemplary embodiment, the data can be obtained from remote locations and analyzed at a different location. It is also noted that a wide variety of data output utilization or transfer techniques can be utilized. By way of example only and not by way of limitation, in an exemplary embodiment, some of the teachings detailed herein can be utilized to remotely fit a hearing prosthesis. FIG. 13 presents a functional schematic of a system with which some of the teachings detailed herein and/or variations thereof can be implemented. In this regard, FIG. 13 is a schematic diagram illustrating one exemplary arrangement in which a system 1206 can be used to execute one or more or all of the method actions detailed herein in conjunction with the use of a device 100, which can be a hearing prosthesis, or can be a personal computer or a phone, etc. Herein, device 100 will often be referred to as a hearing prosthesis, but note that that can be a proxy for any of the devices that can enable the data acquisition according to the teachings detailed herein. In general, in an exemplary embodiment, the system of FIG. 13 can be representative of both the system utilized to develop the model (to train the model) and the system that results from the model.

System 1206 will be described, at least in part, in terms of interaction with a recipient, although that term is used as a proxy for any pertinent subject to which the system is applicable (e.g., the test subjects used to train the DNN, the subject utilized to validate the trained DNN, the subjects to which methods 200, 400, 1000 and 1100 are applicable, etc.). In an exemplary embodiment, system 1206 is a recipient controlled system while in other embodiments, it is a remote controlled system. In an exemplary embodiment, system 1206 can correspond to a remote device and/or system, which, as detailed above, can be a portable handheld device (e.g., a smart device, such as a smart phone), and/or can be a personal computer, etc.

In an exemplary embodiment, system 1206 can be a system having additional functionality according to the method actions detailed herein. In the embodiment illustrated in FIG. 13, the device 100 can be connected to system 1206 to establish a data communication link 1208 between the hearing prosthesis 100 (where hearing prosthesis 100 is a proxy for any device that can enable the teachings detailed herein, such as a smartphone with a microphone, a dedicated microphone, a phone, etc.) and system 1206. System 1206 is thereafter bidirectionally coupled by a data communication link 1208 with hearing prosthesis 100. Any communications link that will enable the teachings detailed herein that will communicably couple the implant and system can be utilized in at least some embodiments.

System 1206 can comprise a system controller 1212 as well as a user interface 1214. Controller 1212 can be any type of device capable of executing instructions such as, for example, a general or special purpose computer, a handheld computer (e.g., personal digital assistant (PDA)), digital electronic circuitry, integrated circuitry, specially designed ASICs (application specific integrated circuits), firmware, software, and/or combinations thereof. As will be detailed below, in an exemplary embodiment, controller 1212 is a processor. Controller 1212 can further comprise an interface for establishing the data communications link 1208 with the hearing prosthesis 100 (again, which is a proxy for any device that can enable the methods herein—any device with a microphone and/or with an input suite that permits the input data for the methods herein to be captured). In embodiments in which controller 1212 comprises a computer, this interface may be, for example, internal or external to the computer. For example, in an exemplary embodiment, controller 1206 and cochlear implant may each comprise a USB, FireWire, Bluetooth, Wi-Fi, or other communications interface through which data communications link 1208 may be established. Controller 1212 can further comprise a storage device for use in storing information. This storage device can be, for example, volatile or non-volatile storage, such as, for example, random access memory, solid state storage, magnetic storage, holographic storage, etc.

User interface 1214 can comprise a display 1222 and an input interface 1224 (which, in the case of a touchscreen of the portable device, can be the same). Display 1222 can be, for example, any type of display device, such as, for example, those commonly used with computer systems. In an exemplary embodiment, element 1222 corresponds to a device configured to visually display a plurality of words to the recipient 1202 (which includes sentences), as detailed above.

Input interface 1224 can be any type of interface capable of receiving information from a recipient, such as, for example, a computer keyboard, mouse, voice-responsive software, touchscreen (e.g., integrated with display 1222), microphone (e.g. optionally coupled with voice recognition software or the like) retinal control, joystick, and any other data entry or data presentation formats now or later developed. It is noted that in an exemplary embodiment, display 1222 and input interface 1224 can be the same component, e.g., in the case of a touch screen). In an exemplary embodiment, input interface 1224 is a device configured to receive input from the recipient indicative of a choice of one or more of the plurality of words presented by display 1222.

It is noted that in at least some exemplary embodiments, the system 1206 is configured to execute one or more or all of the method actions detailed herein, where the various sub-components of the system 1206 are utilized in their traditional manner relative to the given method actions detailed herein.

In an exemplary embodiment, the system 1206, detailed above, can execute one or more of the actions detailed herein and/or variations thereof automatically, at least those that do not require the actions of a recipient.

While the above embodiments have been described in terms of the portable handheld device obtaining the data, either directly from the recipient or from the hearing prosthesis, and performing a given analysis, as noted above, in at least some exemplary embodiments, the data can be obtained at a location remote from the recipient, and thus the device 100. In such an exemplary embodiment, the system 1206 can thus also include the remote location (e.g., clinic).

In this vein, it is again noted that the schematic of FIG. 13 is functional. In some embodiments, a system 1206 is a self-contained device (e.g., a laptop computer, a smart phone, etc.) that is configured to execute one or more or all of the method actions detailed herein and/or variations thereof. In an alternative embodiment, system 1206 is a system having components located at various geographical locations. By way of example only and not by way of limitation, user interface 1214 can be located with the recipient (e.g., it can be the portable handheld device 240) and the system controller (e.g., processor) 1212 can be located remote from the recipient. By way of example only and not by way of limitation, the system controller 1212 can communicate with the user interface 1214, and thus the portable handheld device 240, via the Internet and/or via cellular communication technology or the like. Indeed, in at least some embodiments, the system controller 1212 can also communicate with the user interface 1214 via the Internet and/or via cellular communication or the like. Again, in an exemplary embodiment, the user interface 1214 can be a portable communications device, such as, by way of example only and not by way of limitation, a cell phone and/or a so-called smart phone. Indeed, user interface 1214 can be utilized as part of a laptop computer or the like. Any arrangement that can enable system 1206 to be practiced and/or that can enable a system that can enable the teachings detailed herein and/or variations thereof to be practiced can be utilized in at least some embodiments.

Figure 14:
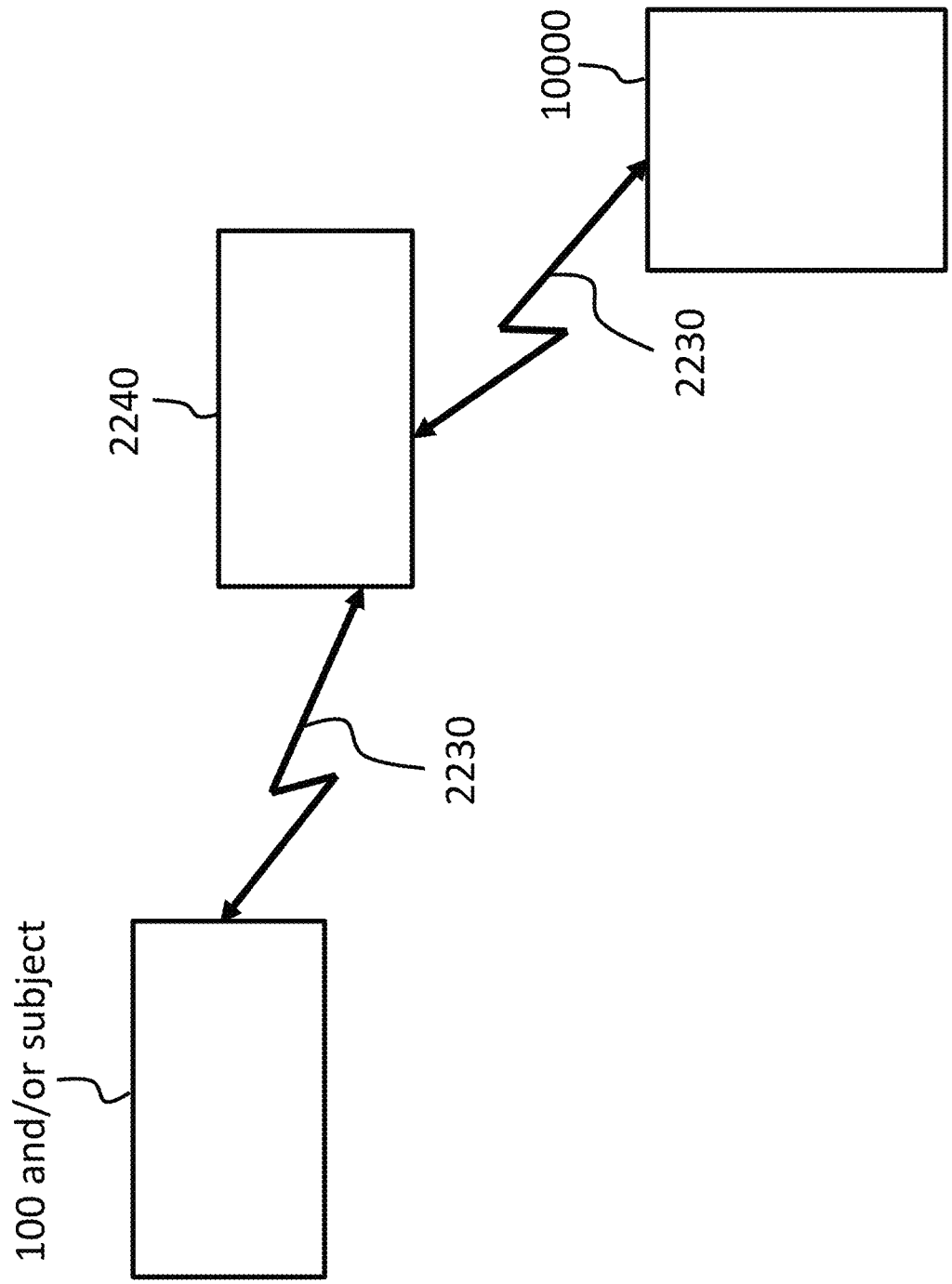
FIG. 14 depicts a schematic functionally representing another exemplary system.

In view of the above, FIG. 14 depicts an exemplary functional schematic, where a device 2240, which will be detailed herein in this exemplary embodiment as a portable hand-held device 2240, but is to be understood as representative of any device that can enable the teachings detailed herein (e.g., remote dedicated hearing prosthesis control unit, personal computer, smartphone, landline phone, etc.) is in communication with a geographically remote device/facility 10000 via link 2230, which can be an internet link. The geographically remote device/facility 1000 can encompass controller 1212, and the remote device 240 can encompass the user interface 1214. The geographic remote device/facility 10000 can be the clinic. It is also noted that in the embodiment of FIG. 18, link 2230 can represent communication between the portable handheld device 2240 and the hearing prosthesis 100 and/or can represent communication between the portable handheld device 2240 and the subject (bypassing the hearing prosthesis).

Accordingly, an exemplary embodiment entails executing some or all of the method actions detailed herein where the recipient of the hearing prosthesis or other subject, the hearing prosthesis 100 and/or the portable handheld device 2240 is located remotely (e.g., geographically distant) from where at least some of the method actions detailed herein are executed.

In an exemplary embodiment, the portable handheld device 2240 is configured to execute one or more of the method actions detailed herein. In an exemplary embodiment, the portable handheld device 2240 is configured to communicate with the cloud as detailed above and/or with the clinic as detailed above.

Reference herein is frequently made to the recipient of a hearing prosthesis. It is noted that in at least some exemplary embodiments, the teachings detailed herein can be applicable to a person who is not the recipient of a hearing prosthesis. Accordingly, for purposes of shorthand, at least some exemplary embodiments include embodiments where the disclosures herein directed to a recipient correspond to a disclosure directed towards a person who is not a recipient but instead is only hard of hearing or otherwise has a hearing ailment.

Any disclosure herein of the hearing prosthesis executing one or more of the method actions detailed herein are having a disclosed functionality also corresponds to a disclosure of a remote device and/or a person executing those method actions. That is, by way of example only and not by way of limitation, the actions of the hearing prosthesis can be performed by another device, such as a smart phone, a personal computer, etc. Also, any disclosure of any remote device executing one or more the method actions detailed herein or otherwise having a disclosed functionality also corresponds to a disclosure of a hearing prosthesis having such functionality and/or being configured to execute such method actions, along with a disclosure of a person executing such method actions.

Any disclosure of any method action detailed herein corresponds to a disclosure of a device and/or a system for executing that method action. Any disclosure of any method of making an apparatus detailed herein corresponds to a resulting apparatus made by that method. Any functionality of any apparatus detailed herein corresponds to a method having a method action associated with that functionality. Any disclosure of any apparatus and/or system detailed herein corresponds to a method of utilizing that apparatus and/or system. Any feature of any embodiment detailed herein can be combined with any other feature of any other embodiment detailed herein providing that the art enables such, and it is not otherwise noted that such is not the case.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. A method, comprising:
obtaining hearing data and speech data for a statistically significant number of individuals; and
analyzing with a processor the obtained hearing data and speech data using machine learning to develop a predictive algorithm for hearing loss, wherein the predictive algorithm predicts hearing loss based on input indicative of speech of a hearing impaired person who is not an individual of the statistically significant number of individuals.

2. The method of claim 1, wherein:
the predictive algorithm is not focused on a specific speech feature.

3. The method of claim 1, wherein:
analyzing with the processor the obtained hearing data and speech data using machine learning to develop a predictive algorithm for hearing loss results in a developed predictive algorithm for hearing loss; and
wherein analyzing the obtained hearing data machine-trains a system that results in the developed predictive algorithm for hearing loss.

4. The method of claim 1, wherein:
the obtaining hearing data and speech data results in obtained hearing data and speech data; and
of the obtained hearing data and speech data, a first portion thereof is used, in a neural network, for training and a second portion thereof is used, in the neural network, for verification.

5. The method of claim 1, wherein:
the machine learning develops the predictive algorithm by internally identifying features from the obtained hearing data and speech data.

6. The method of claim 1, wherein:
the predictive algorithm utilizes a complex arrangement number of features present in the obtained speech data to predict hearing loss.

7. The method of claim 1, wherein:
the method further comprises:
obtaining biographical data for individuals of the statistically significant number of individuals, wherein obtaining biographical data for the individuals of the statistically significant number of individuals results in obtained biographical data; and
analyzing with the processor the obtained hearing data and speech data and the obtained biographical data using a neural network to develop the predictive algorithm for hearing loss, wherein the predictive algorithm predicts hearing loss based on input indicative of speech and biographical data of a hearing impaired person who is not an individual of the statistically significant number of individuals.

8. The method of claim 1, wherein:
the predictive algorithm is a trained system trained based on the statistically significant number of individuals.

9. The method of claim 1, wherein:
the predictive algorithm utilizes non-heuristic processing to predict the hearing loss.

10. The method of claim 1, further comprising:
developing a prescription and/or a fitting regime for a hearing prosthesis to be used by a user using the predictive algorithm.

11. The method of claim 10, further comprising:
utilizing a code written in language of a neural network to develop the prescription and/or fitting regime.

12. The method of claim 10, wherein:
the prescription is developed based on relationships as opposed to correlations between speech and hearing loss.

13. The method of claim 1, wherein:
the predictive algorithm is agnostic to speech features.

14. The method of claim 10, further comprising obtaining the input indicative of speech of a hearing impaired person who is not one of the individuals of the statistically significant number of individuals, wherein developing the prescription and/or the fitting regime is executed directly from the input indicative of speech of a hearing impaired person who is not one of the individuals of the statistically significant number of individuals.

15. The method of claim 10, further comprising:
- obtaining non-speech and non-hearing related data and developing the prescription and/or fitting regime based on the non-speech and non-hearing related data.

16. The method of claim 1, further comprising:
- obtaining the input indicative of speech of the hearing impaired person who is not one of the individuals of the statistically significant number of individuals, wherein the input indicative of speech of a hearing impaired person who is not one of the individuals of the statistically significant number of individuals was developed without identified speech feature correlation to the hearing loss of the hearing impaired person who is not one of the individuals of the statistically significant number of individuals.

17. The method of claim 1, wherein:
- the predictive algorithm is a trained neural network.

18. The method of claim 1, further comprising:
- obtaining biographical data of the hearing impaired person who is not one of the individuals of the statistically significant number of individuals, wherein a result is that there is obtained biographical data;
- obtaining speech data of the hearing impaired person; and
- analyzing with the processor the speech data of the hearing impaired person and the obtained biographical data using the predictive algorithm to develop data regarding hearing loss of the hearing impaired person.

* * * * *